United States Patent
Vaughan, Jr. et al.

(10) Patent No.: US 11,864,863 B2
(45) Date of Patent: Jan. 9, 2024

(54) SYSTEM, METHOD AND COMPUTER-ACCESSIBLE MEDIUM FOR ACCELERATED, SIMULTANEOUS QUANTITATIVE AND NON-SYNTHETIC MULTI-CONTRAST IMAGING

(71) Applicants: John Thomas Vaughan, Jr., New York, NY (US); Sairam Geethanath, New York, NY (US); Sachin Jambawalikar, New York, NY (US); Pavan Poojar, New York, NY (US); Enlin Qian, New York, NY (US)

(72) Inventors: John Thomas Vaughan, Jr., New York, NY (US); Sairam Geethanath, New York, NY (US); Sachin Jambawalikar, New York, NY (US); Pavan Poojar, New York, NY (US); Enlin Qian, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 17/475,687

(22) Filed: Sep. 15, 2021

(65) Prior Publication Data
US 2022/0071490 A1    Mar. 10, 2022

Related U.S. Application Data

(63) Continuation of application No. PCT/US2020/022996, filed on Mar. 16, 2020.
(Continued)

(51) Int. Cl.
A61B 5/00    (2006.01)
A61B 5/055    (2006.01)
(Continued)

(52) U.S. Cl.
CPC ............ *A61B 5/0042* (2013.01); *A61B 5/055* (2013.01); *G01R 33/561* (2013.01); *G01R 33/5602* (2013.01)

(58) Field of Classification Search
CPC .. A61B 5/0042; A61B 5/055; G01R 33/5602; G01R 33/561
See application file for complete search history.

(56) References Cited

U.S. PATENT DOCUMENTS

| 2014/0085318 A1 | 3/2014 | Nadar et al. |
| 2017/0007148 A1 | 1/2017 | Kaditz et al. |

(Continued)

FOREIGN PATENT DOCUMENTS

WO    2018/108643 A1    6/2018

OTHER PUBLICATIONS

International Search Report and Written Opinion dated Jun. 15, 2020 for International Patent Application No. PCT/US2020/022996.
(Continued)

*Primary Examiner* — Gregory H Curran
(74) *Attorney, Agent, or Firm* — Hunton Andrews Kurth LLP

(57) ABSTRACT

An exemplary system, method, and computer-accessible medium for generating a particular image which can be a quantitative image(s) of at least one section(s) of a patient(s) or (ii) a non-synthetic contrast image(s) of the section(s) of the patient(s), can include, for example, generating a first magnetic resonance (MR) signal and detecting the first MR signal to patient(s), receiving a second MR signal from the patient(s) that can be based on the first MR signal, and generating the particular image(s) based on the second MR signal. The first MR signal can be a configured MR signal. The configured MR signal can be configured for a particular
(Continued)

contrast. The first MR signal can have a constant signal intensity. The first MR signal can be generated based on a degree of a plurality of flip angles that maintains the constant signal intensity. A degree of flip angles can be selected for the first MR signal based on the particular contrast.

19 Claims, 19 Drawing Sheets

Related U.S. Application Data

(60) Provisional application No. 62/819,159, filed on Mar. 15, 2019.

(51) Int. Cl.
    *G01R 33/56*             (2006.01)
    *G01R 33/561*           (2006.01)

(56) References Cited

U.S. PATENT DOCUMENTS

2017/0082715 A1    3/2017    Choi et al.
2018/0217220 A1*  8/2018    Gulani .............. G01R 33/5676

OTHER PUBLICATIONS

Communication Pursuant to Rules 70(2) and 70a(2) EPC dated Dec. 1, 2022 for European Patent Application No. 20773478.1.
European Extended Search Report dated Nov. 14, 2022 for European Patent Application No. 20773478.1.
Imam Shaik et al.: "Tailored Magnetic Resonance Fingerprinting: optimizing acquisition schedule and intelligent reconstruction using a block approach", Proceedings of the International Society for Magnetic Resonance in Medicine, ISMRM, Joint Annual Meeting ISMRM-ESMRMB, Paris, France, Jun. 16-21, 2018.
Bhairav Bipin Mehta et al: "Magnetic resonance fingerprinting: a technical review : Magnetic Resonance in Medicine", Magnetic Resonance in Medicine, vol. 81, No. 1, Sep. 14, 2018.
Qian Enlin et al: "Tailored magnetic resonance fingerprinting for simultaneous non-synthetic and quantitative imaging: A repeatability study", Medical Physics., vol. 49, No. 3, Jan. 27, 2022.
Yankeelov TE, Abramson RG, Quarles CC. Quantitative multimodality imaging in cancer research and therapy. Nat. Rev. Clin. Oncol. 2014;11:670-680.
Abramson R, Burton K, John-Paul J, radiology ES-A, 2015 undefined. Methods and challenges in quantitative imaging biomarker development. Elsevier.
Doran SJ. Chapter 21 Quantitative magnetic resonance imaging: applications and estimation of errors. Data Handl. Sci. Technol. 1996;18:452-488 doi: 10.1016/S0922-3487(96)80058-X.
Jara H. Theory of quantitative magnetic resonance imaging.
Seow P, et al. "Quantitative magnetic resonance imaging and radiogenomic biomarkers for glioma characterisation: a systematic review." Br. J. Radiol. 2018;91:20170930 doi: 10.1259/bjr. 20170930.
Deoni SCL, et al. "Rapid combinedT1 andT2 mapping using gradient recalled acquisition in the steady state." Magn. Reson. Med. 2003;49:515-526 doi: 10.1002/mrm.10407.
Frost R, et al. "Scan time reduction for readout-segmented EPI using simultaneous multislice acceleration: Diffusion-weighted imaging at 3 and 7 Tesla" Magn. Reson. Med. 2015;74:136-149 doi: 10.1002/mrm.25391.
Shukla-Dave A, Obuchowski NA, Chenevert TL, et al. Quantitative imaging biomarkers alliance (QIBA) recommendations for improved precision of DWI and DCE-MRI derived biomarkers in multicenter oncology trials. J. Magn. Reson. Imaging 2018 doi: 10.1002/jmri. 26518.
Tanenbaum LN, Tsiouris AJ, Johnson AN, et al. Synthetic MRI for clinical neuroimaging: results of the Magnetic Resonance Image Compilation (MAGiC) prospective, multicenter, multireader trial. Am. J. Neuroradiol. 2017.
Gonçalves F, Serai S, . . . GZMR, 2018 undefined. Synthetic Brain MRI: Review of Current Concepts and Future Directions. journals. lww.com.
Ma D, Gulani V, Seiberlich N, et al. Magnetic resonance fingerprinting. Nature 2013 doi: 10.1038/nature11971.
Jiang Y, Ma D, Seiberlich N, Gulani V, Griswold MA. MR fingerprinting using fast imaging with steady state precession (FISP) with spiral readout. Magn. Reson. Med. 2015;74:1621-1631 doi: 10.1002/ mrm.25559.
Virtue P, Tamir JI, Doneva M, Yu SX, Lustig M. Learning Contrast Synthesis from MR Fingerprinting.
Hänicke W, Vogel HU. An analytical solution for the SSFP signal in MRI. Magn. Reson. Med. 2003;49:771-775 doi: 10.1002/mrm. 10410.
Bernstein M a., King KF, Zhou XJ. Handbook of MRI Pulse Sequences, Appendix II.; 2004. doi: 10.1016/B978-012092861-3/ 50026-1.
Weigel M. Extended phase graphs: Dephasing, RF pulses, and echoes—pure and simple. J. Magn. Reson. Imaging 2015;41:266-295 doi: 10.1002/jmri.24619.
Cao X, Liao C, Wang Z, et al. Robust sliding-window reconstruction for Accelerating the acquisition of MR fingerprinting. Magn. Reson. Med. 2017;78:1579-1588 doi: 10.1002/mrm.26521.
Fessler J. Image reconstruction toolbox. Available at website http:// www.eecs.umich.edu /fessler/code 2012 doi: 10.1007/978-0-387-85922-4.
Dixon WT. Simple proton spectroscopic imaging. Radiology 1984;153:189-194 doi: 10.1148/radiology.153.1.6089263.
Wansapura JP, Holland SK, Dunn RS, Ball WS. NMR relaxation times in the human brain at 3.0 tesla. J. Magn. Reson. Imaging 1999;9:531-538 doi: 10.1002/(SICI)1522-2586(199904)9:4<531::AID-JMRI4>3.0.CO;2-L.
Reeder SB, Mckenzie CA, Pineda AR, et al. Water-fat separation with IDEAL gradient-echo imaging. J. Magn. Reson. Imaging 2007;25:644-652 doi: 10.1002/jmri.20831.).
Ravi, K. S., Geethanath, S., & Vaughan, J. T. (2018b). lmr-framework for rapid design and deployment of non-cartesian sequences. In I2i workshop. Retrieved from cai2r.net/i2i.
Ravi, K. et al. (2018). Pulseq graphical programming interface: Open source visual environment for prototyping pulse sequences and integrated magnetic resonance imaging algorithm development. Magnetic resonance imaging, 52, 9-15. doi:10.1016/j.mri.2018.03. 008.
Smith SM, Jenkinson M, Woolrich MW, et al. Advances in functional and structural MR image analysis and implementation as FSL. Neuroimage 2004;23:S208-S219 doi: 10.1016/J.NEUROIMAGE. 2004.07.051.
Ravi, K. S., Geethanath, S., Jochen, W., & Vaughan, J. T. (2018a). MR value driven autonomous mri using imr-framework. In ISMRM workshop on machine learning part ii, Washington, D.C.
Ravi, K. S., Potdar, S., Poojar, P., Reddy, A. K., Kroboth, S., Nielsen, J.-F., Zaitsev, M., et al. (2018). Pulseq graphical programming interface: Open source visual environment for prototyping pulse sequences and integrated magnetic resonance imaging algorithm development. Magnetic resonance imaging, 52, 9-15. doi: 10.1016/j.mri.2018.03.008.

* cited by examiner

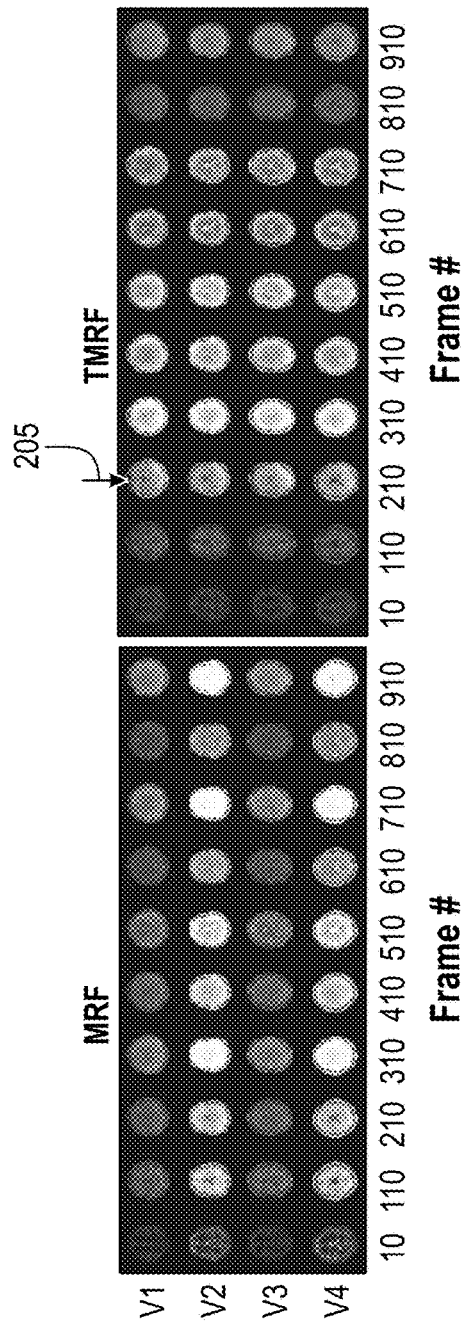
Figure 2A
Figure 2B
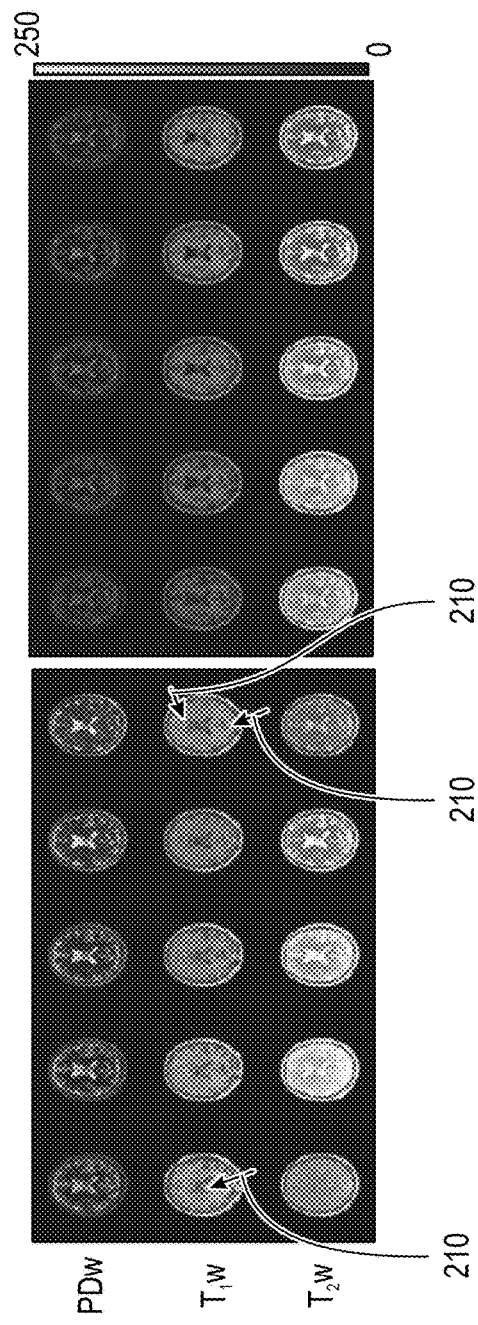
Figure 2C
Figure 2D

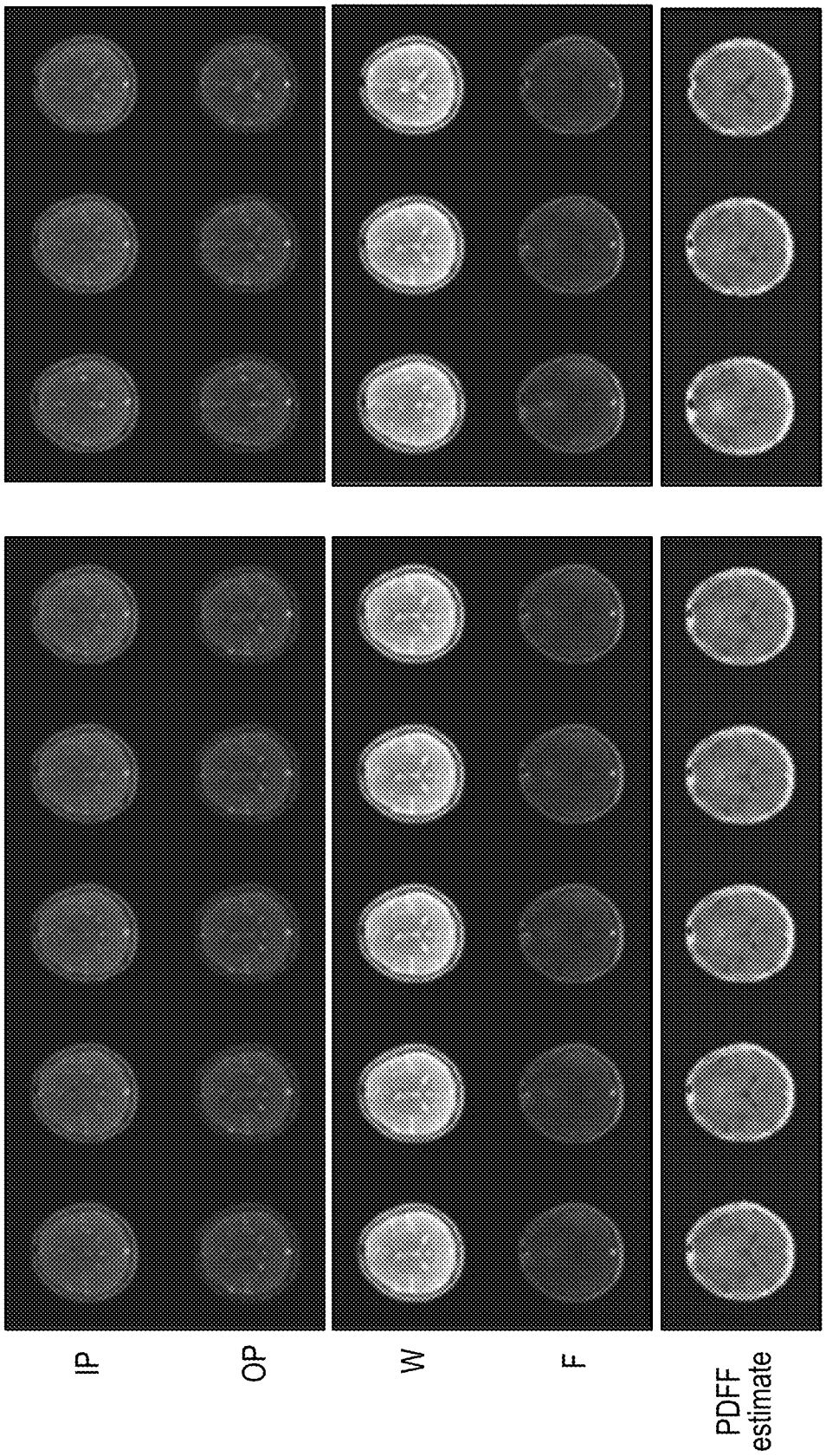

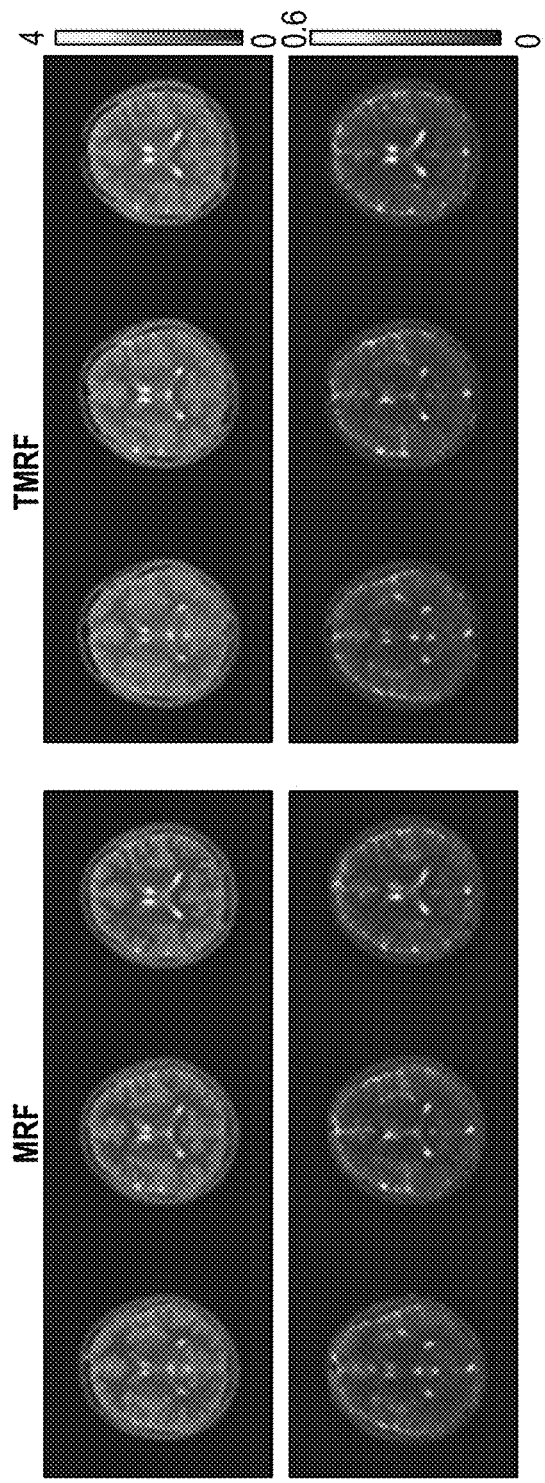
Figure 8A
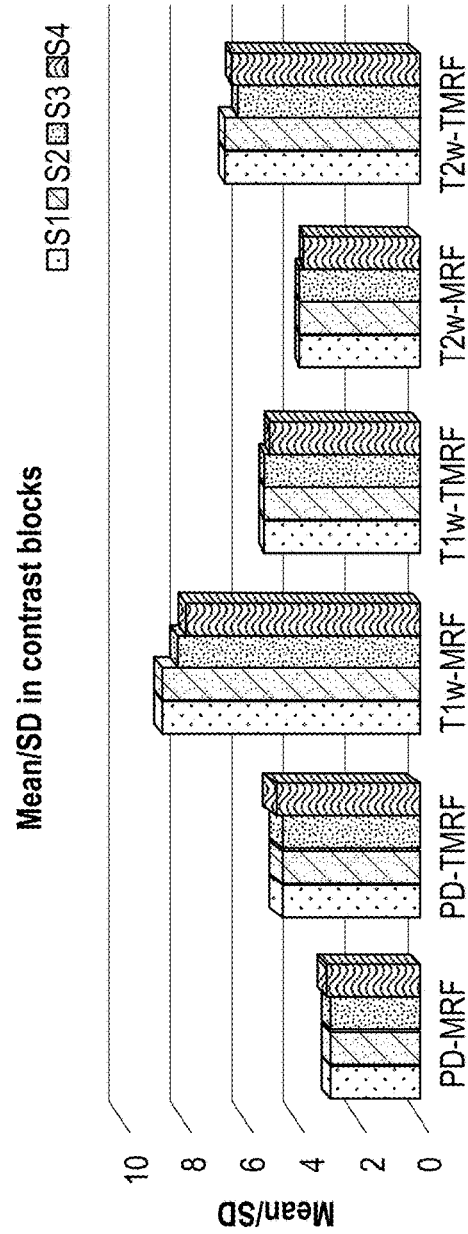
Figure 8B
Figure 8C

SYSTEM, METHOD AND COMPUTER-ACCESSIBLE MEDIUM FOR ACCELERATED, SIMULTANEOUS QUANTITATIVE AND NON-SYNTHETIC MULTI-CONTRAST IMAGING

CROSS-REFERENCE TO RELATED APPLICATION(S)

This application is a continuation of International Patent Application No. PCT/US2020/022996, filed on Mar. 16, 2020, that published as International Patent Publication No. WO 2020/190879 on Sep. 24, 2020, and also relates to and claims priority from U.S. Provisional Patent Application No. 62/819,159, filed on Mar. 15, 2019, the entire disclosures of all of which are incorporated herein by reference.

FIELD OF THE DISCLOSURE

The present disclosure relates generally to magnetic resonance imaging, and more specifically, to exemplary embodiments of exemplary system, method and computer-accessible medium for accelerated, simultaneous quantitative and non-synthetic multi-contrast imaging.

BACKGROUND INFORMATION

The role of quantitative magnetic resonance imaging ("qMRI") is well established. (See, e.g., Reference 1-5). Typically, this involves acquiring data from multiple acquisitions to facilitate a regression analysis. This results in prolonged acquisition times, specifically in the case of multi-parametric magnetic resonance imaging ("MRI") to obtain maps of relaxation (see, e.g., Reference 6), diffusion (see, e.g., References 7 and 8), pharmacokinetic parameters (see, e.g., Reference 8), etc. Synthetic MRI in general (see, e.g., References 9 and 10), and MR Fingerprinting ("MRF") (see, e.g., References 11 and 12), in particular mitigate this challenge by simultaneously acquiring data for multiple parametric maps (e.g., $T_1$, $T_2$, etc.). However, one issue can be the unavailability of contrast images routinely obtained from conventional imaging protocols. Synthetically generated contrast images can be derived from MRF reconstructed parametric maps. However, it can be challenging to estimate the multitude of phase terms involved in the MR signal equation (see, e.g., Reference 13), resulting from diffusion, flow, susceptibility, off-resonance, etc. Recently, a deep learning based MRF reconstruction approach directly reconstructing contrast images from MRF data has been reported. (See, e.g., Reference 14). This work overcomes challenges with simulation model limitations and associated artifacts. It assumes that the routinely obtained training data can be the ground truth. However, these images can also be "synthetically" generated based on MRF data and training data, rather than from new data directly, and have not been explored in the cases of pathology. Thus, the performance of such methods can significantly depend on the variety, volume and veracity of training data.

Thus, it may be beneficial to provide the exemplary system, method and computer-accessible medium for an accelerated, simultaneous quantitative and non-synthetic multi-contrast imaging which can overcome at least some of the deficiencies described herein above.

SUMMARY OF EXEMPLARY EMBODIMENTS

To overcome these limitations, the exemplary system, method, and computer-accessible medium, according to an exemplary embodiment of the present disclosure, can be used for simultaneous, natural (e.g., non-synthetic), multi-contrast and quantitative MR imaging through tailoring of the MRF acquisition schedule.

Ab exemplary system, method, and computer-accessible medium for generating a particular image which can be a quantitative image(s) of at least one section(s) of a patient(s) or (ii) a non-synthetic contrast image(s) of the section(s) of the patient(s), can include, for example, generating a first magnetic resonance (MR) signal and directing the first MR signal to patients(s), receiving a second MR signal from the patient(s) that can be based on the first MR signal, and generating the particular image(s) based on the second MR signal. The first MR signal can be a configured MR signal. The configured MR signal can be configured for a particular contrast. The first MR signal can have a constant signal intensity. The first MR signal can be generated based on a degree of a plurality of flip angles that maintains the constant signal intensity. A degree of flip angles can be selected for the first MR signal based on the particular contrast.

In some exemplary embodiments of the present disclosure, the degree of the flip angles can vary within a particular range. The degree of the flip angles can vary about a mean value. The degree of the flip angles can vary monotonously about the mean value. The degree of the flip angles can vary pseudo randomly within the particular range. The particular range can be about −5+/−4 degrees, about 45+/−5 degrees, about 75+/−5 degrees, or about 75+/−5 degrees. The particular contrast can include T1, T2, proton density, water, fat, off resonance, diffusion, perfusion, or flow. The non-synthetic contrast image(s) can be a non-synthetic multi-contrast image(s). The particular image(s) can be generated using a reconstruction procedure. The reconstruction procedure can be a sliding window reconstruction procedure. The reconstruction procedure can include converting the second MR signal to an image using a Non-Uniform Fast Fourier Transform.

In certain exemplary embodiments of the present disclosure, MR information can be generated based on the second MR signal by pre-processing the second MR sign by compensating for a calibrated gradient delay, scaling k-space of the second MR signal with a ratio of a filed of view to a matrix size, removing spikes in the second MR signal, and weighting k-space data in the second MR signal with a predetermined density compensation factor, where the particular image(s) can be generated based on the MR information. The particular image(s) can be generated by vector-dot product matching $L_2$-norm normalized dictionary entries with voxel signal evolutions in the second MR signal.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 2A is a set of exemplary images of a mid-volume slice of four volunteers magnetic resonance fingerprint acquired over 1000 frames according to an exemplary embodiment of the present disclosure;

FIG. 2B is a set of exemplary images of tailored magnetic resonance fingerprint depicting proton density contrast and T1 contrast according to an exemplary embodiment of the present disclosure;

FIG. 2C is a set of exemplary images of contrast windows according to an exemplary embodiment of the present disclosure;

FIG. 2D is a set of exemplary images of plots for tailored magnetic resonance fingerprint according to an exemplary embodiment of the present disclosure;

FIGS. 7A and 7B are exemplary water-fat images using the exemplary TMRF according to an exemplary embodiment of the present disclosure;

FIGS. 8A and 8B are exemplary quantitative images according to an exemplary embodiment of the present disclosure;

FIG. 8C is an exemplary graph illustrating the comparison of the mean to standard deviation in each of the contrast blocks according to an exemplary embodiment of the present disclosure;

Figure 1A:
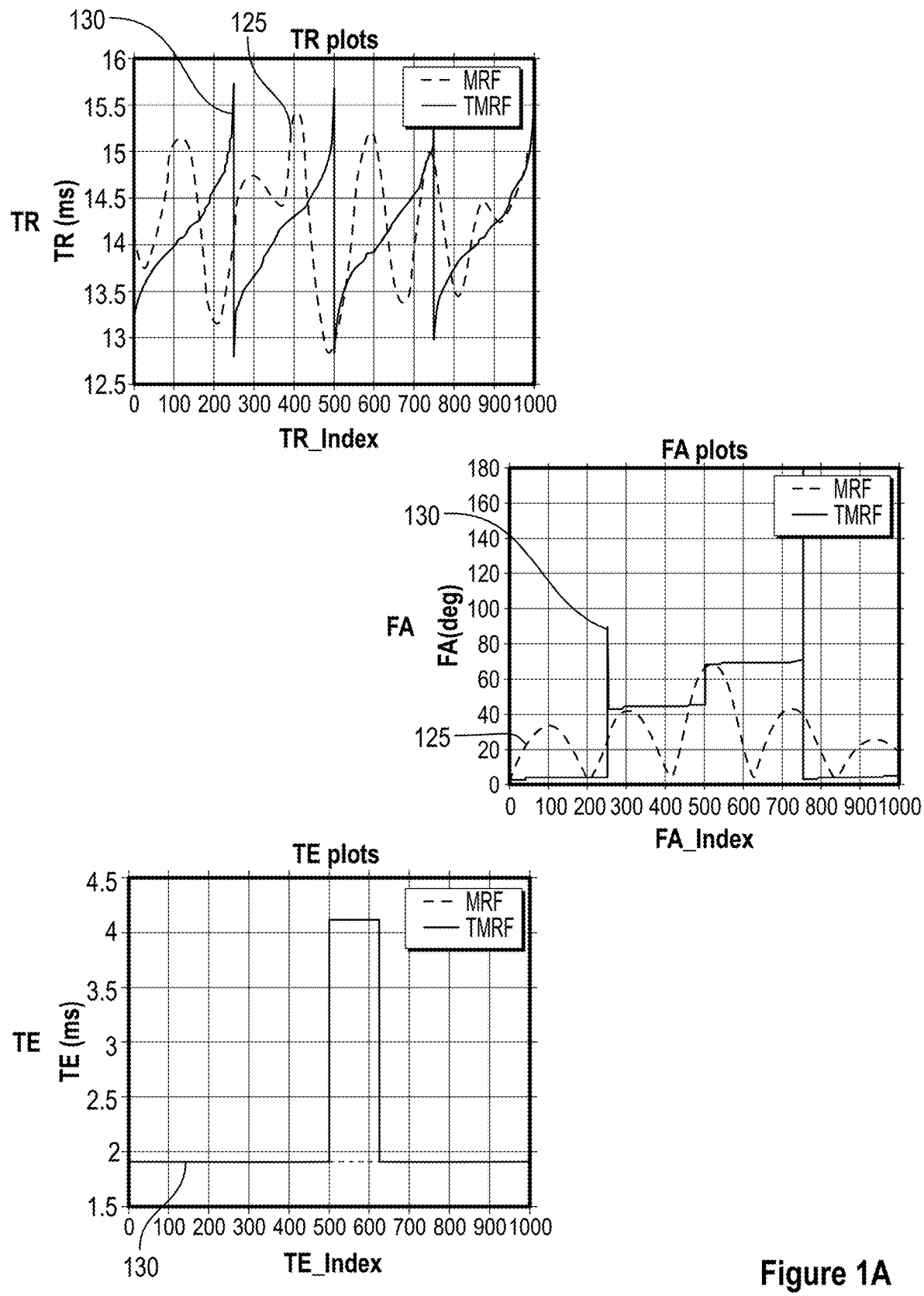
FIG. 1A is a set of exemplary graphs illustrating a tailored magnetic resonance fingerprint design for TR, FA and TE values according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is one so in connection with the illustrative embodiments and is not limited by the particular embodiments illustrated in the figures and the appended claims.

DETAILED DESCRIPTION OF EXEMPLARY EMBODIMENTS

Figure 1B:
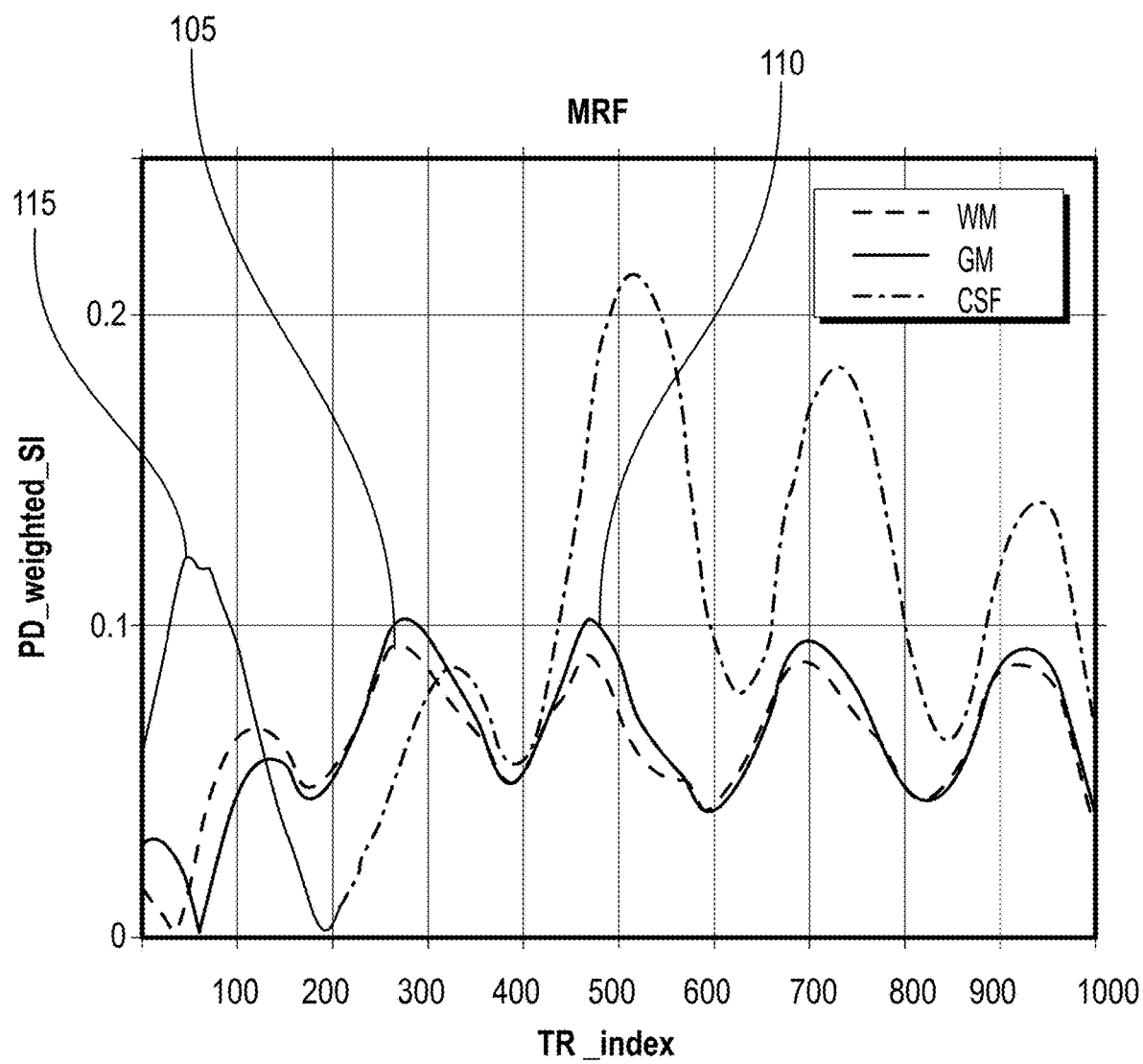
FIG. 1B is an exemplary graph illustrating Extended Phase Graph simulations of the magnetic resonance fingerprint acquisition schedules from white matter, gray matter, and cerebrospinal fluid according to an exemplary embodiment of the present disclosure.

A steady state free precession ("SSFP") sequence can be provided with a thousand spiral readouts designed to derive image signal evolutions for different tissue matters. MR image contrast derived from such a sequence an be modulated more by the flip angle than the repetition time. (see, e.g., References 13, 15 and 16, and FIGS. 1A and 1B). FIG. 1A shows a set of exemplary graphs illustrating a tailored magnetic resonance fingerprint design for TR, FA, and TE values according to an exemplary embodiment of the present disclosure. FIG. 1B shows an exemplary graph illustrating Extended Phase Graph simulations of the magnetic resonance fingerprint acquisition schedules from white matter, gray matter, and cerebrospinal fluid according to an exemplary embodiment of the present disclosure. This has been shown by MRF to significantly vary flip angles while restricting the TR to a much smaller range above the minimum TR achievable. Further, MR signal simulation tools such as Extended Phase Graph ("EPG") (see, e.g., Reference 17)) can be leveraged to vary signal intensities of tissue matters based on their properties (e.g., $T_1$, $T_2$, etc.) in "blocks" of time. Also, the signal intensities of these tissue matters can remain relatively constant, or slowly varying, if the flip angles were varied smoothly, monotonously, and in a small range within one block. Magnetization preparation in the form of an inversion pulse can be efficiently utilized to include suppression of short and long relaxation components like fat and liquids at different temporal points. This tissue matter dependent tailored design choice can facilitate different relaxation contrast "windows", signal constancy in a given contrast window, and a meaningful sliding window reconstructed signal intensity image. The exemplary approach, referred to as the Tailored MRF ("TMRF") can retain the MRF derived qMRI benefits of generating multiple parametric maps simultaneously. In comparison, the MRF sequence includes oscillations in flip angle resulting in corresponding fluctuating signal evolution. Sliding window reconstruction of non-synthetic signal intensity images can be challenging due to the highly undersampled acquisition and the superposition of highly varying signal intensities.

Exemplary Methods

Figure 1C:
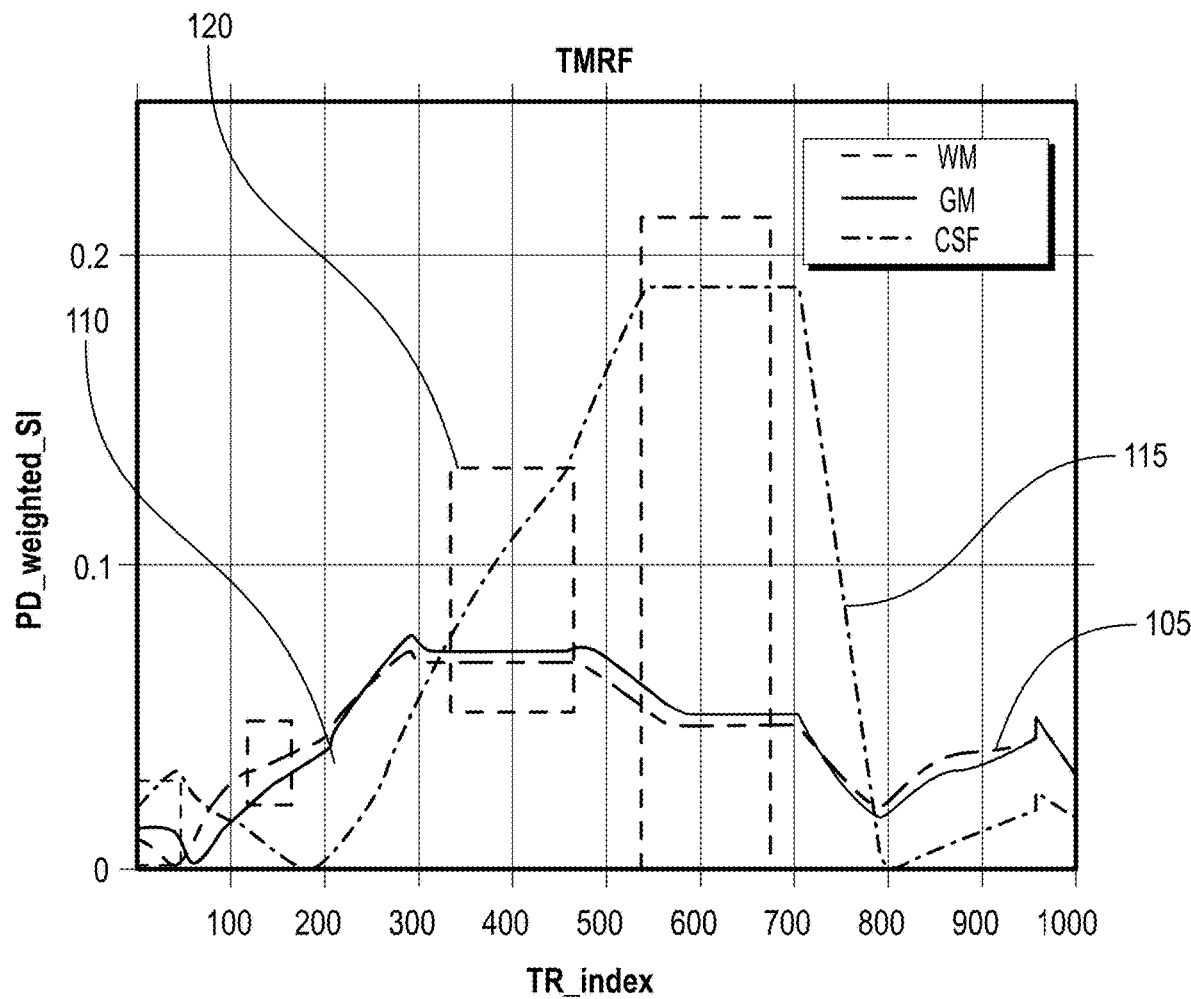
FIG. 1C is an exemplary graph illustrating Extended Phase Graph simulation for tailored magnetic resonance fingerprint with targeted windows according to an exemplary embodiment of the present disclosure.

Exemplary Tailored acquisition design and dictionary generation: A one thousand time point (e.g., frames) MRF schedule was used to tailor the magnetization evolution of three tissue types: White Matter ("WM"), Gray Matter ("GM") and Cerebrospinal Fluid ("CSF"). This was performed by designing acquisition blocks targeting one or more contrast windows in each block. In this exemplary implementation, three acquisition blocks for (i) PD and $T_1$ contrast windows; (ii) $T_2$ plus flow contrast window; and (iii) $T_2$ contrast window were generated. Each block facilitated a total of 250 frames (e.g., block size). Each block was generated by choosing different Flip Angles ("FA") with the minimum TR (e.g., 12.8 ms) possible: $5^6$ for PD and $T_1$, $45^6$ for $T_2$ and flow, $70^6$ for $T_2$ weighting. These values were determined based on SSFP literature (see, e.g., References 13, 15 and 16), and EPG simulations. These FA values can be referred to as base FAs for each of the contrast blocks. In each of the three cases, a normally distributed noise with a zero mean and a standard deviation of 0.5 was added to the minimum TR and the base FAs. These two vectors were then sorted in ascending order to avoid spike like transients in the magnetization evolution. FIG. 1C shows an exemplary graph illustrating Extended Phase Graph simulations for TMRP with targeted windows according to an exemplary embodiment of the present disclosure. A $90^6$ pulse was introduced at the $250^{th}$ frame (e.g., end of PD and $T_1$ acquisition block) to facilitate constant signal intensities during the $T_2$ plus flow contrast window (e.g., shown in boxes 920 in FIG. 1C between the $250^{th}$ to $500^{th}$ frame). A fourth block (e.g., Frame #751 to 1000) included repeated values from the first block. This was performed to match the length of the MRF schedule. The values of TE were chosen to be the minimum (e.g., 1.908 ms) except in frames between 500 and 625 (e.g., Dixon contrast window). In this contrast window, the TE was increased by 2.2 ms to facilitate an out of phase acquisition. The reading TR, FA and TE vectors for the three blocks were concatenated to form the TR/FA/TE schedule. These TMRF parameters in comparison to the corresponding MRF schedule (see, e.g., Reference 12) are shown in FIG. 1A, which illustrates TR, FA and TE values for the 1000 frame acquisition for MRF (e.g., lines 925) and TMRF (e.g., lines 930), the TR and FA plot depict the acquisition "blocks" of length 250 frames. EPG was used to simulate the magnetization evolution dictionary for a range of $T_1$ (e.g., 0 to 4000 ms in steps of 20 ms) and $T_2$ (e.g., 0 to 400 ms in steps of 20 ms: 450 to 600 ms in steps of 50 ms; 700 ms to 2000 ms in steps of 500 ms) values. The dictionary was then sliding window reconstructed (see, e.g., Reference 18), with a window length of 89. The simulation was repeated to account for any changes in the minimum TR resulting from the acquisition. Examples of flip angles can include, but is not limited to, to the following: T1=5+/−4 degrees (plus or minus 15%), T2=45+/−5 degrees (plus or minus 15%), T1 Flair=75+/−5 degrees (plus or minus 15%), and Dixon=75+/−5 degrees (plus or minus 15%).

Exemplary MR acquisition: In vivo brain imaging of four healthy volunteers was performed. Each of the volunteers was scanned with the MRF and TMRF schedules with 20 slices (e.g., for whole brain coverage), slice thickness of 5 mm, minimum TR of 12.6-12.8 ms, field of view 225-240 mm in each direction with a final matrix size of 256×256. The slice planning for both sequences per volunteer were maintained the same to facilitate spatial comparisons. Both sequences leveraged an 89-shot spiral with 608-pint readout, maximum gradient strength of 33 mT/m and a maximum slew rate of 120 T/m/s on a 3T GE 750w scanner using an eight-channel head coil. The resulting acquisition times for the MRF and TMRF cases were 5:11 and 4:41 (e.g., minute: seconds) respectively.

Exemplary Reconstruction—non-synthetic contrast images: Raw data for both cases were pre-processed by compensating for a calibrated gradient delay (e.g., 3.5 microseconds in the exemplary case), scaling k-space with the ratio of FOV to matrix size, removal of spikes (e.g., threshold of twice the standard deviation of the FID) and weighting the k-space data with the pre-compared density compensation factor for the 89 shot spiral trajectory. This data was then converted to images using the Non-Uniform Fast Fourier Transform using the image reconstruction toolbox (see, e.g., Reference 19), and complex coil combined and sliding window reconstructed to provide 2D multi-slice images over time.

Exemplary Reconstruction—quantitative maps: $L_2$-norm normalized dictionary entries were vector-dot produce matched with the voxel signal evolutions of the contrast images. The index of maximum match was chosen as the key to the dictionary entries for the values of $T_1$, $T_2$. PD was determined as the ratio of the resulting match (e.g., maximum value) to the norm of the chosen entry. Repeating this process for all voxels provided the spatial maps of the quantitative parameters. The maps from both schedules were compared with the MRF maps as the reference. In addition, Region-Of-Interest ("ROIs") were drawn on the central slice of each of the four volunteers. Three ROIs each for WM, GM and CSF were drawn and their mean and standard deviation computed. For the PDFF maps in the case of TMRF, the In Phase ("IP") and Out o Phase ("OP") images were added and subtracted to yield water-only ("W") and fat-only ("F") images as typically performed in Dixon imaging. (See, e.g., Reference 20). A PDFF map was computed as F/(F+W).

Exemplary ROI analysis: Three ROIs each corresponding to WM, GM and CSF were manually drawn on the central slices (#9) of the four volunteers. The ROI masks were multiplied with the thousand-point time series of contrast images to obtain the mean ROI signal evolution of the three tissue matters for each of the four volunteers for both schedules. These ROI masks were also multiplied with the parametric maps to obtain mean $T_1$, $T_2$ and PD values for each volunteer. A mean of means was then computed for the $T_1$, $T_2$ values for MRF and the TMRF schedules for the three tissue matters.

Exemplary Results

Figure 1D:
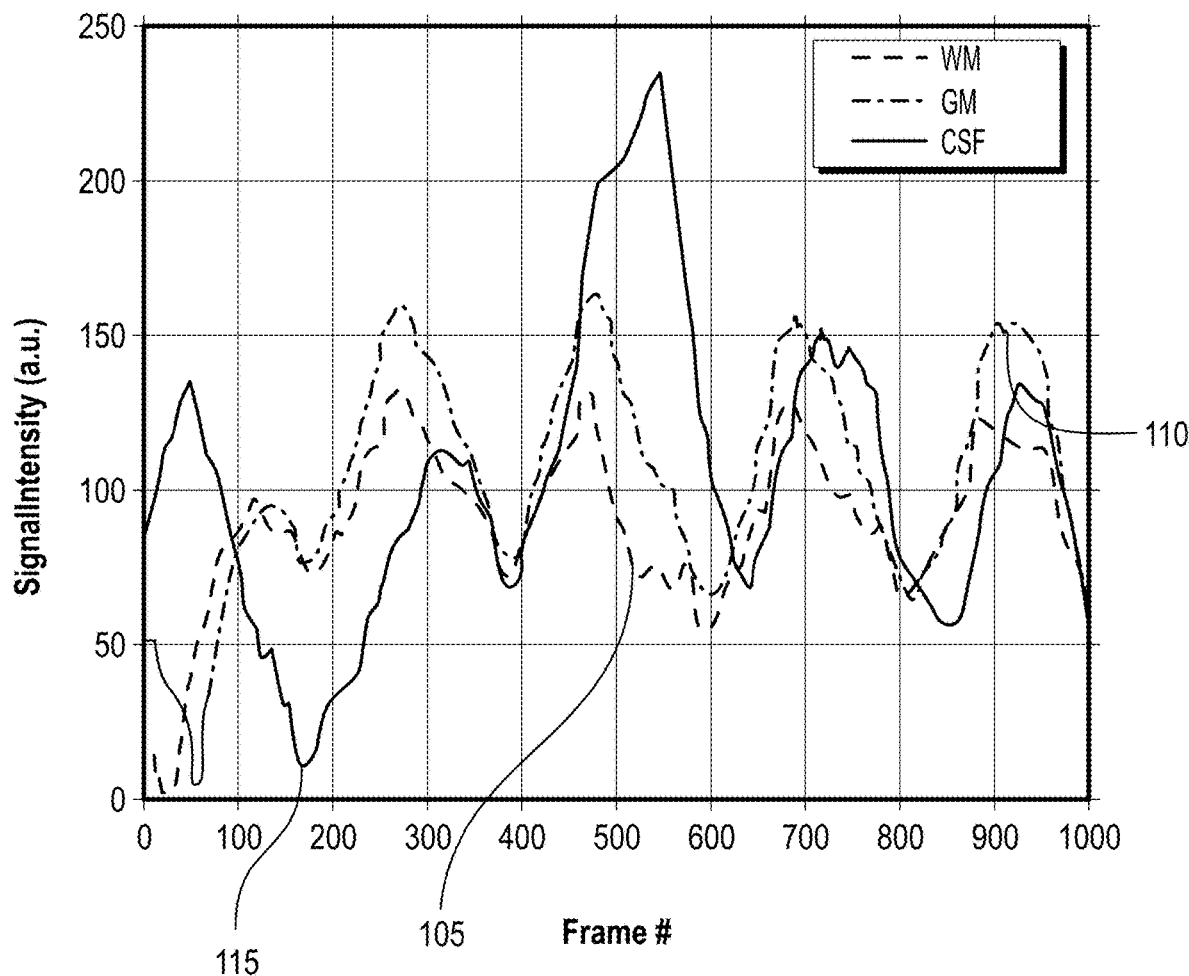
FIG. 1D is an exemplary graph illustrating three voxels for white matter, gray matter and cerebrospinal fluid from a representative magnetic resonance fingerprint acquired in vivo according to an exemplary embodiment of the present disclosure.
Figure 1E:
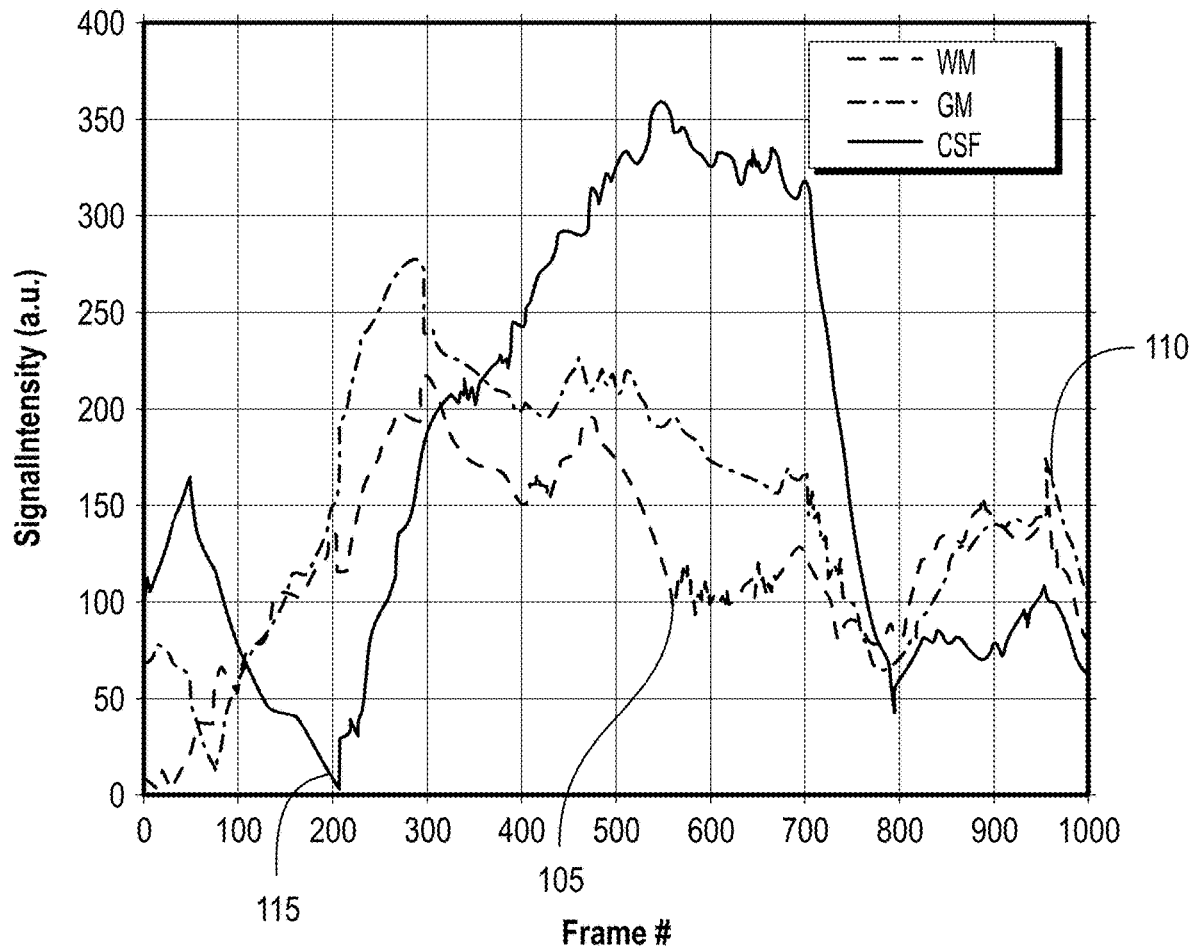
FIG. 1E is an exemplary graph illustrating data voxel plots for tailored magnetic resonance fingerprint according to an exemplary embodiment of the present disclosure.

Exemplary Acquisition schedule design and simulation: FIGS. 1B and 1C show representative MRF and TMRF sliding window simulated signal evolutions for the three tissue types of WM shown by line 905 ($T_1$=850 ms, $T_3$=80 ms for simulation), GM shown by line 910 ($T_1$1330 ms, $T_2$=110 ms) and CSF shown by line 915 ($T_1$4500 ms, $T_2$=1700 ms). TMRF signal evolutions have blocks of slowly varying magnitude compared to MRF, shown by dashed boxes 920. FIG. 1D illustrates representative sliding window reconstructed signal evolutions from three voxels belonging to three tissue types from a volunteer brain data for the MRF case. Exemplary plots from the corresponding voxel locations for TMRF are shown in FIG. 1E. The representative voxel data follow the simulation predictions. The reduction in variation of the TMRF signal evolutions can be easily observed.

Exemplary Non-synthetic MRI reconstruction—temporal and spatial profiles; The sliding window reconstructed central slice for each of the four volunteers for every 100 frames starting with the $10^{th}$ frame is shown in FIG. 2A. In particular, FIG. 2A shows the mid-volume slice of the four volunteers MRF acquired data over 1000 frames with an interval of 100 frames depicting the changes in contrast over time. FIG. 2A shows the different, non-synthetic, contrast that can be derived from TMRF (e.g., frame #10—PD; frame #110—$T_1$ weighting with CSF suppression, frame #610 for $T_1$ weightings. It also indicated that the signal strengths varied relatively less across the four volunteers in TMRF as compared to MRF. This can be attributed to the slowly and monotonously increasing values of the TMRF schedule. In the case of the sudden variation at the end of block 1 (e.g., due to the $90^6$ pulse at the $250^{th}$ frame), an aliasing-like artifact was caused shown arrows 210. Given that this frame was not part of the targeted contrast blocks, this artifact was ignored. Furthermore, the illustrations of FIG. 2B shows five adjacent frames for the PD, $T_1$ and $T_2$ contrasts for both acquisition procedures for a representative data set. In particular, FIG. 2B shows corresponding illustrations for TMRF depicting PD contrasts at the 10th frame, T1 contrast at the 110th frame, T2 contrast around the 610th frame (e.g., chosen frame for T2 was 575th) and the effect of the 900 pulse on the sliding widow reconstruction shown by arrow 205 on frame 210.

Qualitatively, the exemplary TMRF provides improved contrast for $T_1$PD and $T_2$ with suppressed flow artifacts (e.g., shown by arrows 210 for the MRF case). The CSF suppression and increased contrast can be particularly noticeable in the case of $T_1$ Fluid Attenuated Inversion Recovery ("FLAIR")-like weighting (e.g., the first two frames in FIGS. 2C and 2D). For example, FIG. 2C shows various contrast windows: five frames of the central slice of the representative MRF data set to depict PD contrast with an interval of ten frames between adjacent images, T1w contrast images of the central slice with an interval of 20 frames, T2w contrast images with an interval of 50 frames, with the arrows 210 depicting unsuppressed CSF and blood flow. The relative signal strength of TMRF based $T_2$ weighting can be higher than $T_1$ which in turn can be higher than PD (e.g., shows on the same window level of 0-250 au. in FIG. 2C). This trend can be validated by the simulated and observed voxel signal evaluations for the three tissue types in the top and bottom rows of FIG. 1C. FIG. 2D shows corresponding exemplary plots for TMRF data with identical frame intervals within the contrast windows all shown for a signal intensity range between 0 and 250 a.u.

The SNR of PD weighted ("PDw") images in TMRF can be lesser than the MRF case (e.g., top row in FIGS. 2C and 2D). This can be in line with the simulated response of the TMRF design. The PDw images in both cases can be normalized to unit amplitude for better visualization, but was not performed to demonstrate validation of simulation results and comparison of SNR for all three contrasts. In the case of MRF, the $T_1$ and $T_2$ weighted images have increased signal strength compared to PD as can be validated by FIGS. 1B and 1C. However, the relative signal strengths between $T_1$ and $T_2$ weighted images do not follow a trend as the signal evolution oscillates by design. This also does not facilitate the simple and efficient use of the sliding window reconstruction.

Figures 3A, 3B:
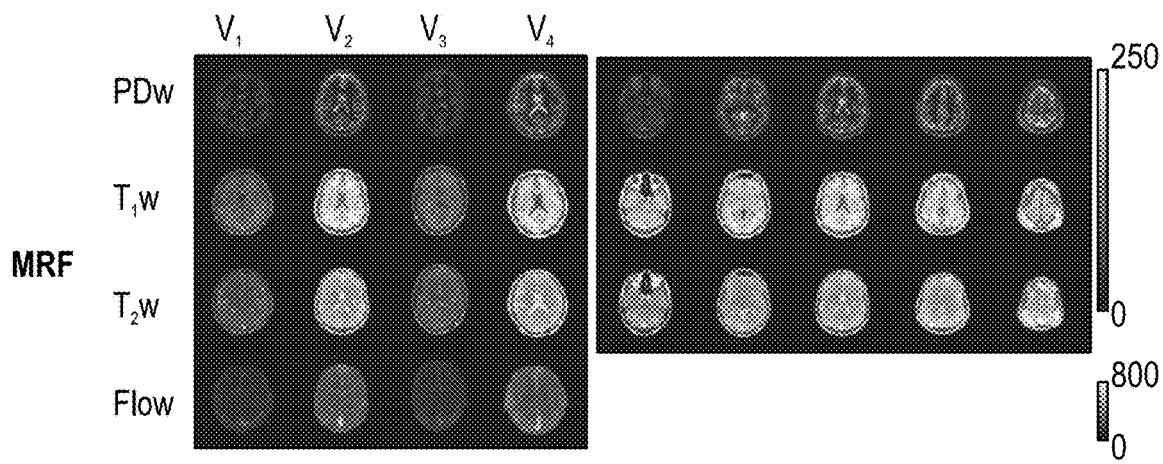
FIG. 3A is a set of exemplary images of mid-volume slices of four volunteers magnetic resonance fingerprint acquired data for PDw, T1w, T2w and flow Maximum Intensity Projection ("MIP") at various contrast window frames according to an exemplary embodiment of the present disclosure.
FIG. 3B is a set of exemplary images of contrast volumes according to an exemplary embodiment of the present disclosure.

FIG. 3A shows a set of exemplary images of mid-volume slices of four volunteers magnetic resonance fingerprint acquired data for PDw, T1w, T2w and flow Maximum Intensity Projection ("MIP") at various contrast window frames according to an exemplary embodiment of the present disclosure. In particular, FIG. 3A shows Mid-volume slice of the four volunteers for MRF acquired data for PDw, T1w, T2w and flow MIP at the chosen contrast window frames of 10, 120, 575 and 410.

Figures 3C, 3D:
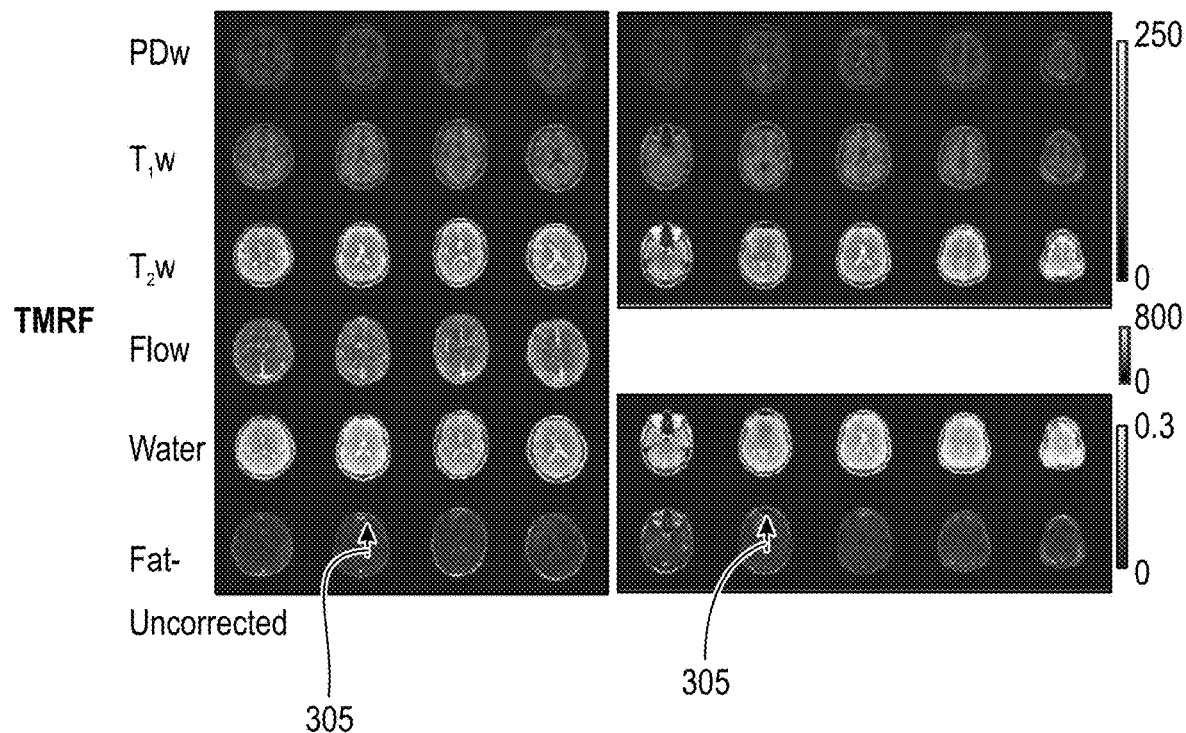
FIG. 3C is a set of exemplary images of tailored magnetic resonance fingerprint contrast windows according to an exemplary embodiment of the present disclosure.
FIG. 3D is a set of exemplary images of contrast volumes from tailored magnetic resonance fingerprint according to an exemplary embodiment of the present disclosure.

FIG. 3B depicts the multiple contrasts obtained from specific temporal points for the central slice of the four volunteers and five equally spaces slices (#1, 5, 9, 13, and 17) out of the twenty slices, with an interval of 4 slices between adjacent images for the representative data set, resulting in full brain coverage for the representative data set. The corresponding TMRF panels shown in FIGS. 3C and 3D qualitatively show improved $T_1$ (e.g., WM>GM) and $T_2$ (e.g., GM>WM) contrast, better CSF suppression for $T_1$ weighted images and higher SNR for flow MIP. For example, FIG. 3C shows TMRF contrast windows in comparison to MRF data shown in FIG. 3A with the additional information of water and uncorrected fat images from frames 450 (in phase) and 575 (out of phase). Arrows 305 show the effect of off-resonance on the uncorrected fat images. FIG. 3D shows corresponding contrast volumes from TMRF acquisitions for the representative data set.

The improved CSF suppression with the exemplary TMRF can be attributed to lower flip angles at the beginning of the schedule following the inversion pulse. The higher SNR for the MIPs can be attributed to the higher flip angles in the second acquisition, such as capturing information related to eyes and any flow component including CSF rather than blood (e.g., vasculature) alone. TMRF panels also show the results of Dixon imaging. The TMRF fat images suffer from off-resonance artifacts shown arrows 305 in FIGS. 3C and 3D.

Figures 4A, 4B:
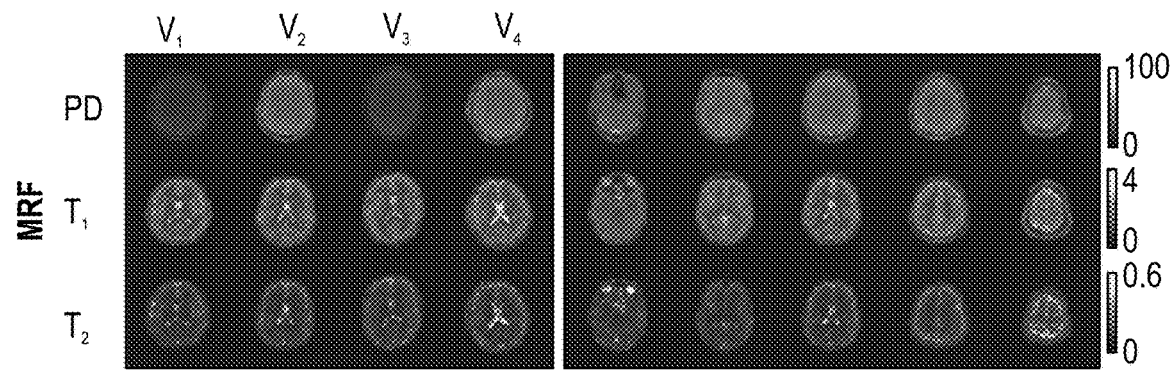
FIG. 4A is a set of exemplary images of mid-volume slices of four volunteers magnetic resonance fingerprint acquired data for proton density, T1, T2 maps according to an exemplary embodiment of the present disclosure.
FIG. 4B is a set of volumes depicted by five slices according to an exemplary embodiment of the present disclosure.
Figures 4C, 4D:
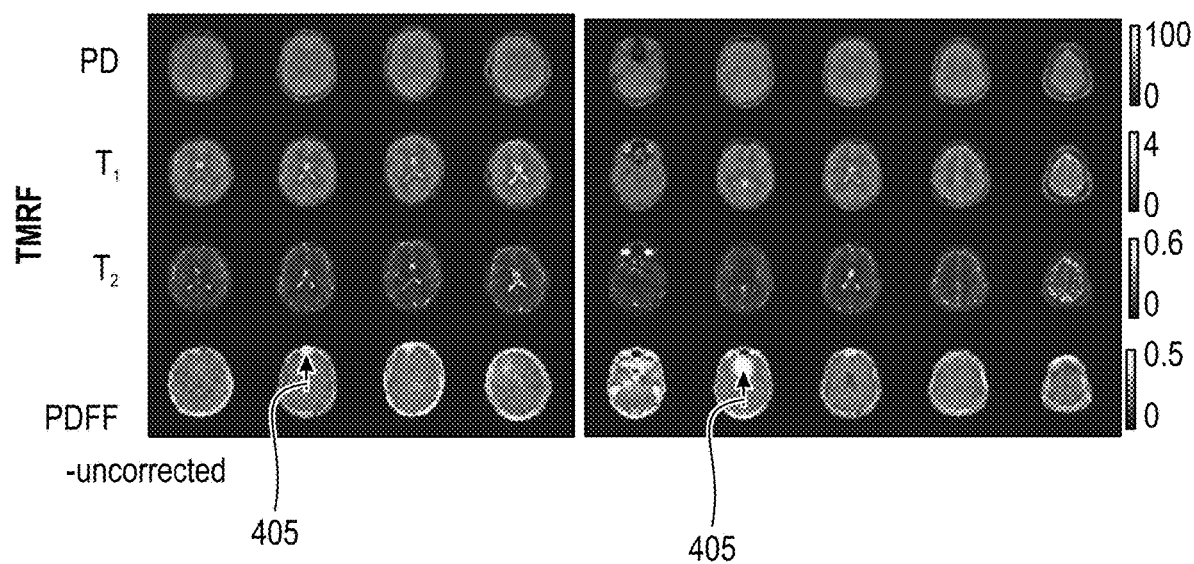
FIG. 4C is a set of exemplary tailored magnetic resonance fingerprint parametric maps according to an exemplary embodiment of the present disclosure.
FIG. 4D is a set of exemplary volumes from tailored magnetic resonance fingerprint acquisition according to an exemplary embodiment of the present disclosure.

Exemplary Reconstruction—quantitative maps: Dictionary matched $T_1$, $T_2$ and PD maps for MRF and TMRF schedules are shown in FIGS. 4A and 4B for the central slice for the four volunteers. For example, FIG. 4A shows mid-volume slices of the four volunteers MRF acquired data for PD, T1, T2 maps. FIG. 4B shows corresponding volumes depicted by five slots with an interval of 4 slices between adjacent images for the representative data set. FIG. 4C shows TMRF parametric maps in comparison to MRF data shown in FIG. 4A with the additional information of uncorrected Proton Density Fat Fraction ("PDFF") map including with arrow 405 pointing to the off-resonance artifact. FIG.

4D shows corresponding exemplary volumes from TMRF acquisitions for the representative data set.

Parametric maps of the five slices for the representative data set shown in FIGS. 2B and 2D are shown in FIGS. 3B and 3D. It can be observed that both approaches result in similar maps and the range of values (e.g., for WM, GM) conform to the literature. (See, e.g., Reference 21). This can be validated qualitatively by the window range and intensities shown. The value of CSF $T_1$ can be much shorter than the literature value and follows values reported in MRF literature. (See, e.g., References 11 and 12). These values can be attributed to flow artifacts and the absence of a longer TR.

Figure 5A:
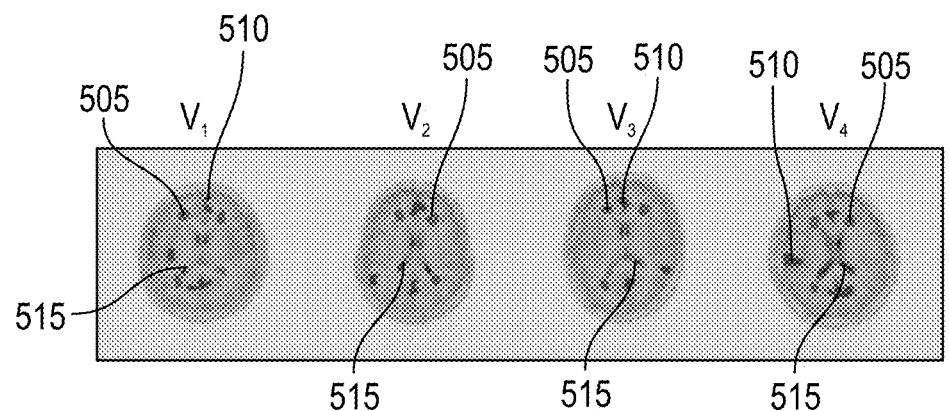
FIG. 5A is a set of exemplary images of mid-volume slices of four volunteers depicting three regions of interest each for white matter, gray matter and cerebrospinal fluid according to an exemplary embodiment of the present disclosure.
Figure 5B:
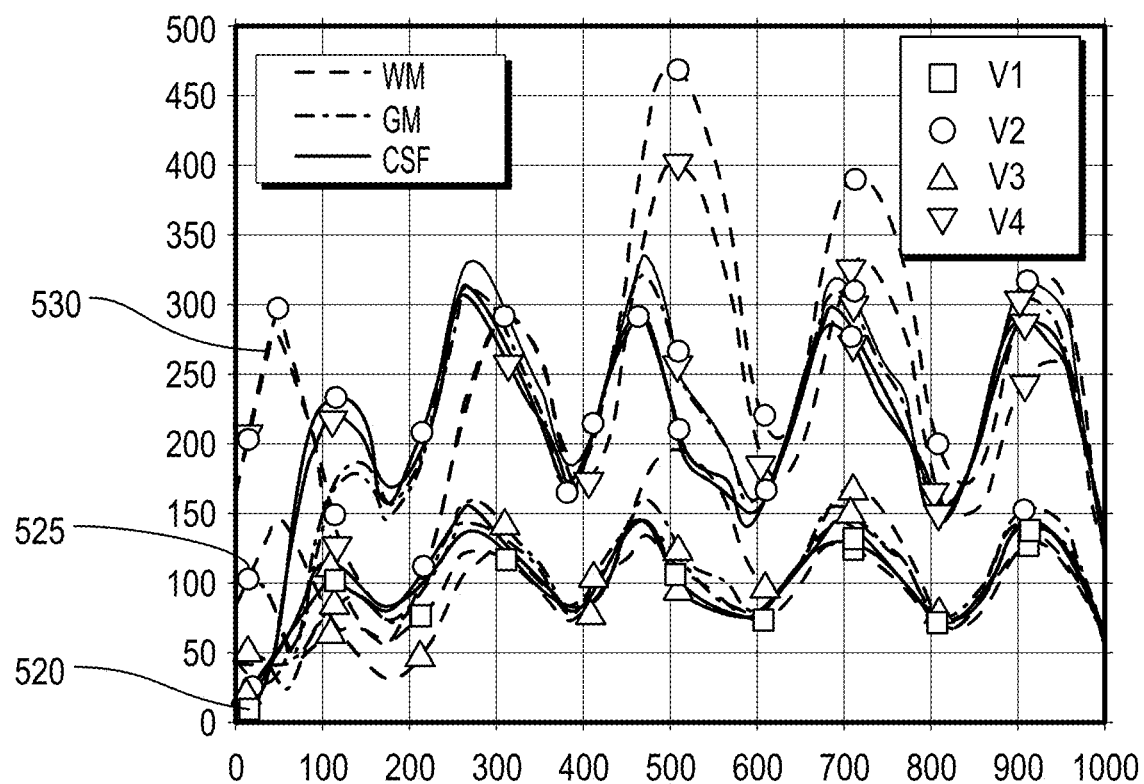
FIG. 5B is an exemplary graph illustrating average signal intensity plots for the regions of interest from FIG. 5A according to an exemplary embodiment of the present disclosure.
Figure 5C:
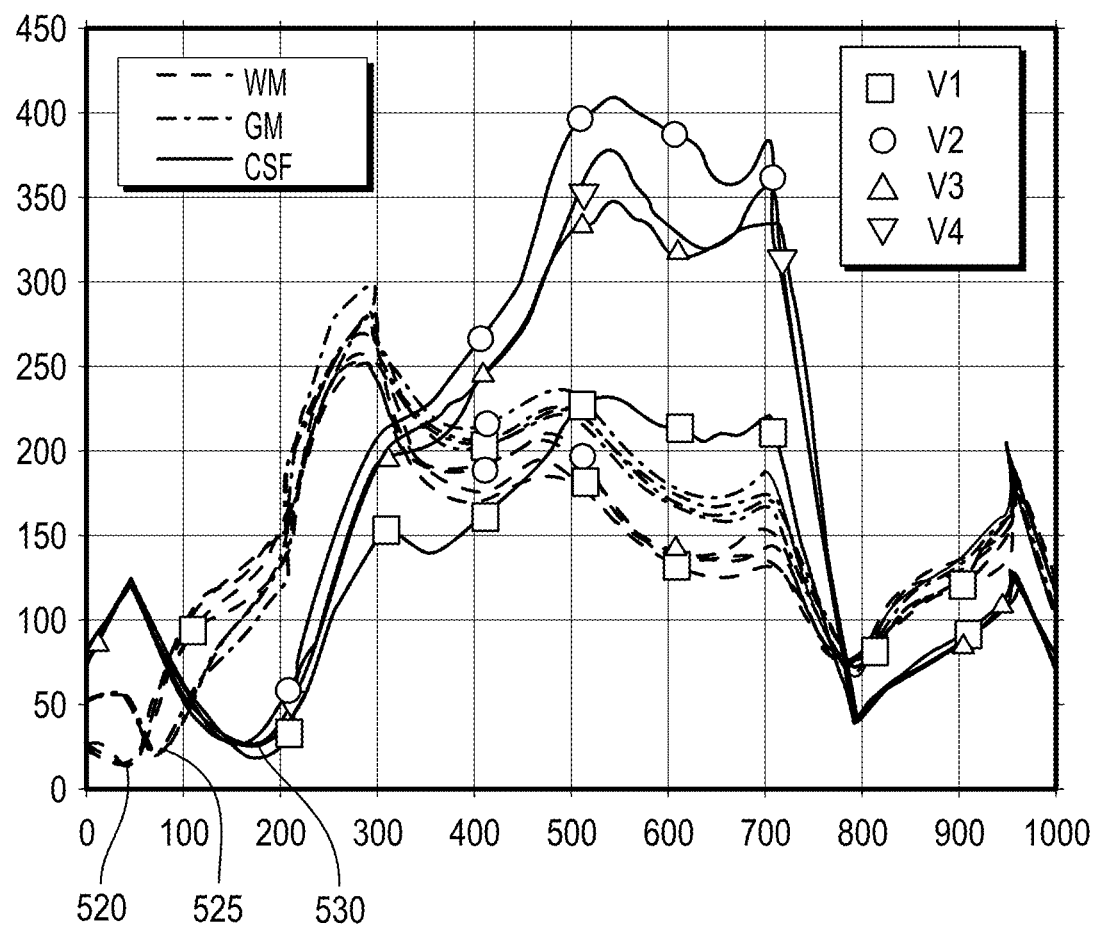
FIG. 5C is an exemplary graph illustrating tailored magnetic resonance fingerprint according to an exemplary embodiment of the present disclosure.
Figure 5D:
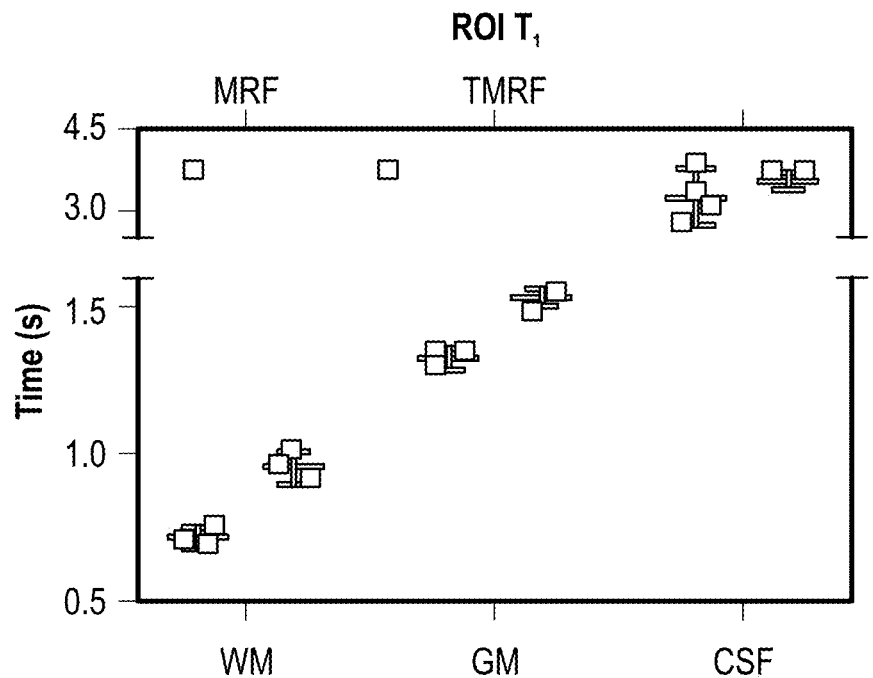
FIG. 5D is an exemplary graph illustrating mean and standard deviation for the three regions of interest from FIG. 5A for T1 maps according to an exemplary embodiment of the present disclosure.
Figure 5E:
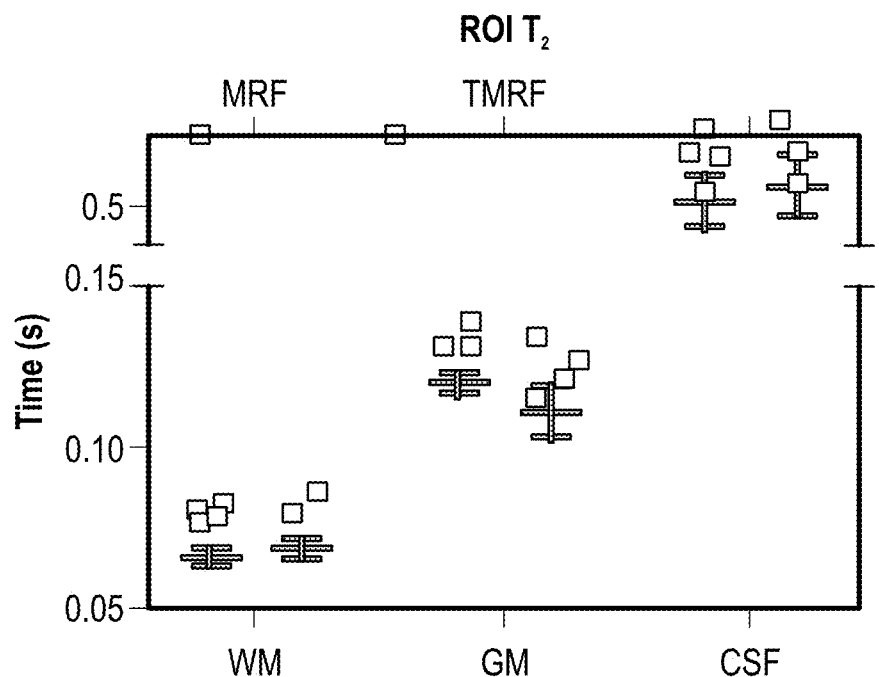
FIG. 5E is an exemplary graph illustrating mean and standard deviation for the three regions of interest from FIG. 5A for T2 maps according to an exemplary embodiment of the present disclosure.

Exemplary ROI analysis: The ROIs drawn on the four volunteers for WM (e.g., areas 505), GM (e.g., areas 510) and CSF (e.g., areas 515) are shown in FIG. 5A. The mean ROI intensity plot over time validated the simulation results shown in FIGS. 1A-1E. These curves can also serve as input to choose appropriate contrast images in the exemplary TMRF. FIG. 5B shows an exemplary graph illustrating average signal intensity plots for the regions of interest (e.g., WM 520, GM 525, and CSF 530) from FIG. 5A according to an exemplary embodiment of the present disclosure. The increased CSF suppression in the first and second acquisition blocks can be seen in FIG. 5C. The mean ROI values for $T_1$ for each volunteer is shown as one datum point in FIG. 5D, resulting in four data points each for the two schedules. The TMRF $T_1$ values for GM and WM can be higher compared to corresponding MRF values. However, these values can be within the range of $T_1$ values reported in literature (e.g., Table 1, (see, e.g., Reference 21)). The mean of means and standard deviation are also shown to demonstrate the close grouping of these observations for each schedule. FIG. 5E shows the corresponding $T_2$ plots for both schedules. The mean ROI values can be closely grouped across volunteers and corresponding values for the two schedules can be similar to one another.

The TMRF schedule can simultaneously produce five different natural contrast images and four quantitative maps. This can facilitate collapsing a traditional protocol into a sequence, reduce acquisition time for multiple parametric maps, and provide radiologists contrast windows to pack images from. The exemplary TMRF provides a simpler and robust alternative to synthetic MRI approaches that can be used for multiple desired contrasts, measurement based and straightforward to reconstruct and visualize. These acquisitions were included to facilitate a comparison with the thousand frame MRF and subsequent dictionary matching operations. Also, the remainder block can be utilized for other contrast, such as diffusion. The inclusion of a $90^6$ pulse at the beginning of the second acquisition block introduced artifacts in sliding window reconstruction, but was utilized to achieve contrast windows in block 2. Therefore, TMRF and MRF schedules can benefit from smoothly varying magnetizations or by eliminating reconstructed images at such transients. The relatively slowly changing magnetization evolutions can be leveraged to assign an effective TR, TE and FA to map them to "contrast images" routinely viewed by the radiologist. For TMRF, the TRs and FAs can be generated based on the mean/base value in each acquisition block as shown in FIG. 1A. The TMRF schedule can facilitate inclusion of Dixon imaging. These corrections can be leveraged from demonstrated methods. (See, e.g., Reference 24). The choice of FA, TR and TE was based on the knowledge of the tissue matters and contrasts for short TRs. An exemplary EPG look ahead procedure (see, e.g., Reference 17), can be utilized to jointly optimize for TMRF contrast between tissue types over time, rather than echo intensities alone.

Figures 6A, 6B, 6C:
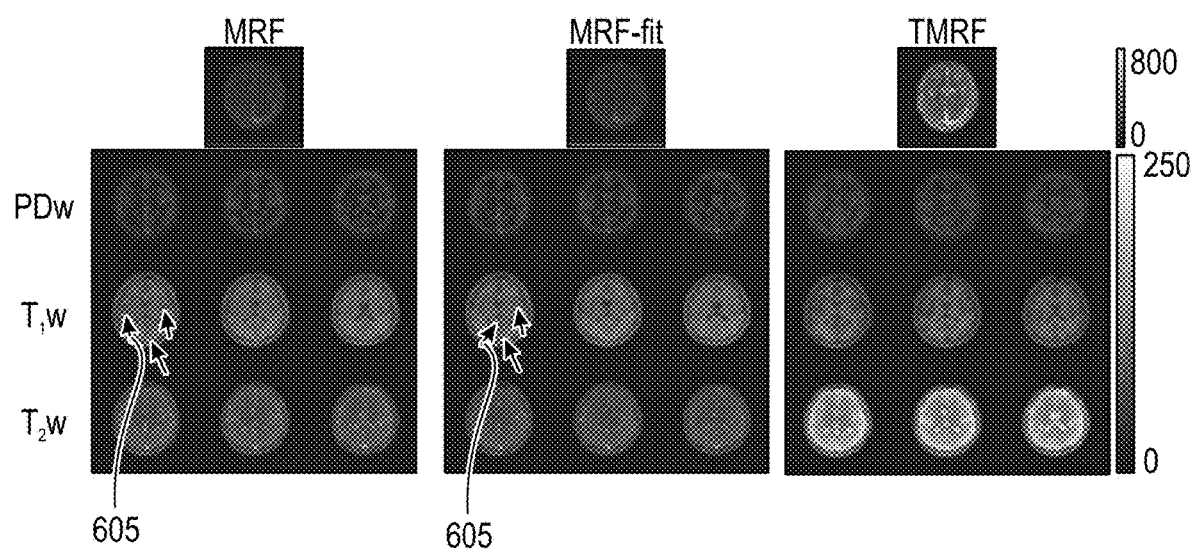
FIGS. 6A-6C are exemplary images of slice(s) of a representative brain data set for three contrasts according to an exemplary embodiment of the present disclosure.

FIGS. 6A-6C show exemplary images of slices of a representative brain data set for three contrasts (e.g., MRF illustrated in FIG. 6A, synthetic images from MRF computed maps shown in FIG. 6B, and the exemplary TMRF reconstructions illustrated in FIG. 6C) according to an exemplary embodiment of the present disclosure. FIG. 6C illustrates the choice of the exemplary flip angle in the T1 block that can facilitate suppression of signals from liquids compared to MRF. The growth of CSF and other liquid-like matters can be facilitated in the exemplary TMRF providing a maximum intensity projection image depicting flow. Additionally, FIG. 6A-6C show that the flow effects can be captured well by the exemplary TMRF. It can be observed that TMRF provides for better T1 contrast without flow artifacts (e.g., arrows 605) as compared to the other two contrasts. The PD and T2 images from the exemplary TMRF can also suppress flow artifacts compared to MRF. The window for all three contrasts are maintained identically in order to compare the relative signal strength for each contrast.

Exemplary Water-Fat Imaging Using TMRF

FIGS. 7A and 7B show exemplary water-fat images using the exemplary TMRF according to an exemplary embodiment of the present disclosure. The top two rows provided in FIG. 7A depict the in and out of phase images for one slice over 5 adjacent time points. FIG. 7B shows these exemplary images for three continuous slices to demonstrate uniform separation across slices. The third and fourth rows in FIGS. 7A and 7B illustrate five frames and the three slices of water and fat images, respectively. These images show the separated fat components along with flow artifacts. The bottom row shows the generated temporal and spatial profiles of the proton density fat fraction map. This information related to water-fat imaging demonstrates the flexibility of the exemplary TMRF to include a desired contrast.

FIGS. 8A and 8B show exemplary quantitative images according to an exemplary embodiment of the present disclosure. In particular, FIG. 8A shows top map T1 and bottom map T2 over three slices for a representative data set computed using MRF. FIG. 8B shows the corresponding maps for the exemplary TMRF. It can be observed that both methods can yield similar maps for T1 and T2, which conforms to previously published literature values. FIG. 8C shows an exemplary graph illustrating the comparison of the mean to standard deviation in each of the contrast blocks according to an exemplary embodiment of the present disclosure. As shown in FIGS. 8A-8C, the exemplary TMRF provides superior mean to standard deviation for PD and T2. This can also observed in FIGS. 2A-2D and FIGS. 6A-6C. T1 contrast from the exemplary TMRF has increased contrast but can have lower mean values, which can be attributed to the decreased signal strength seen from TMRF T1 block.

Exemplary Utility of TMRF Generated Data for Diagnostic Viability

TMRF generated data was validated and optimized in following two steps during the first six months.

Figure 9:
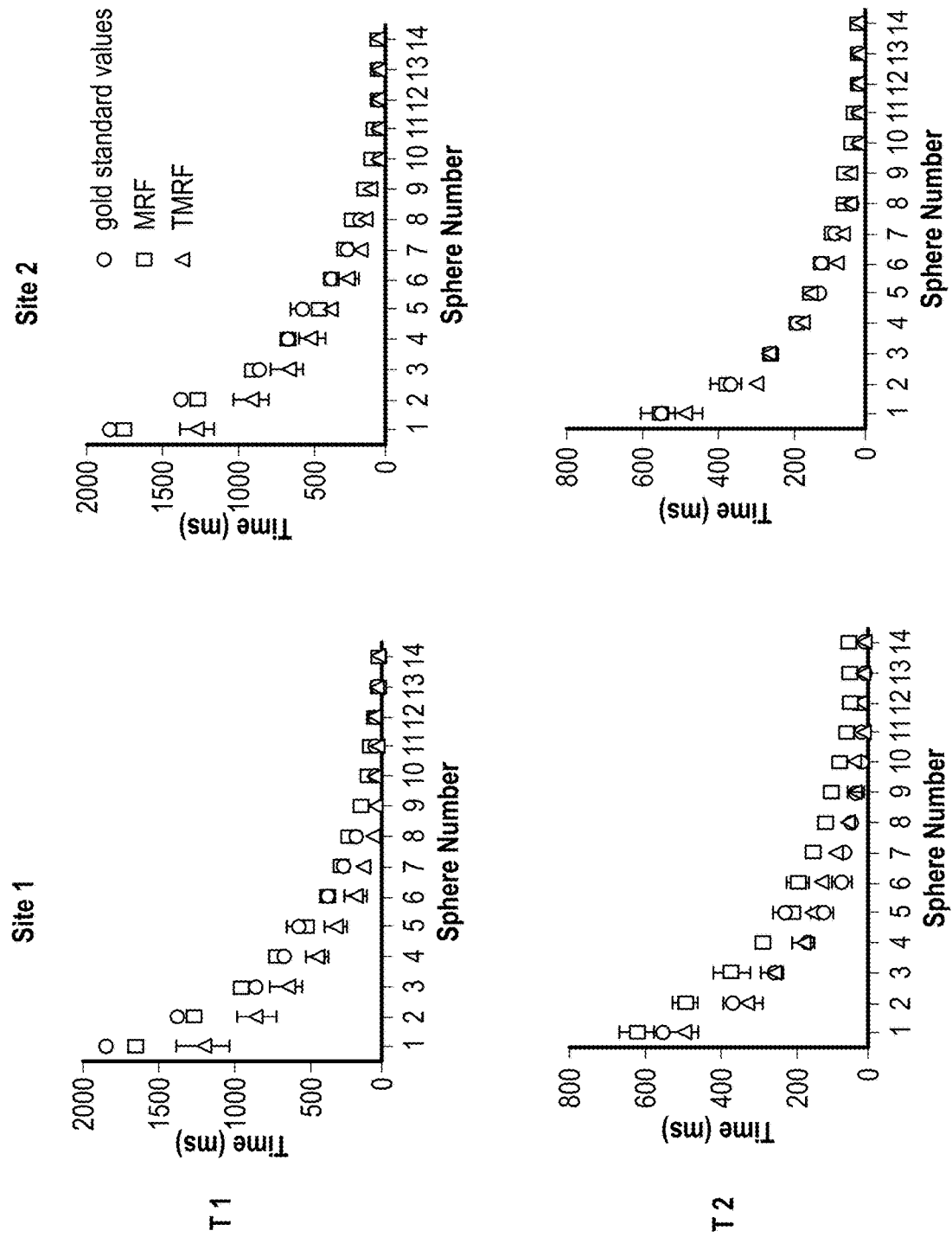
FIG. 9 is a set of exemplary $T_1$ and $T_2$ graph according to an exemplary embodiment of the present disclosure.

Exemplary In Vitro Studies—A two-site repeatability study was performed using the National Institute of Standards and Technology ("NIST") quantitative MRI phantom. The repeatability of $T_1$ and $T_2$ estimation of the exemplary TMRF was compared to MRF and the Gold Standard ("GS") measurements at two sites. The GS included Spin Echo based measurements of $T_1$ and $T_2$. All data was acquired on ISMRM/NIST (QalibreMD Inc., CO, USA) which has three layers of spheres with a large range of $T_1$, $T_2$ and Proton Density values. For in vitro studies, data for 10 days was acquired on phantom using three methods (e.g., GS, MRF and TMRF) at two sites with the same vendor and field strength (e.g., on GE 3T Discovery 750w). GS $T_1$ and $T_2$ measurements were conducted using inversion recovery spin echo ("IRSE") and spin echo ("SE") sequences. The data were reconstructed and matched with an EPG simulated dictionary. ROI analysis was performed to get $T_1$ and $T_2$ estimation for 14 spheres. From the exemplary results, the underestimation of TMRF of long $T_1$ values can be corrected by a constant bias term. For $T_2$ MRF values, site 1 can be close to literature reported values by NIST while site 2 can be close to GS values. The higher order of standard deviation in $T_2$ values can be due to $B_1$ variations. FIG. 9 shows the comparison of $T_1$ map and $T_2$ map obtained from MRF and TMRF across two sites. MRF and TMRF data were averaged from 10-day repeatability scans. The data were obtained from the distinct 14 spheres present in the $T_1$ and $T_2$ plates of ISMRM/NIST phantom (QalibreMD Inc., CO, USA). A manual ROI analysis was performed on eight datasets. 100 pixels were selected for each sphere in $T_1$ maps while 70 pixels were selected for $T_2$ maps due to differences in field of view; MRF and TMRF.

Figure 10:
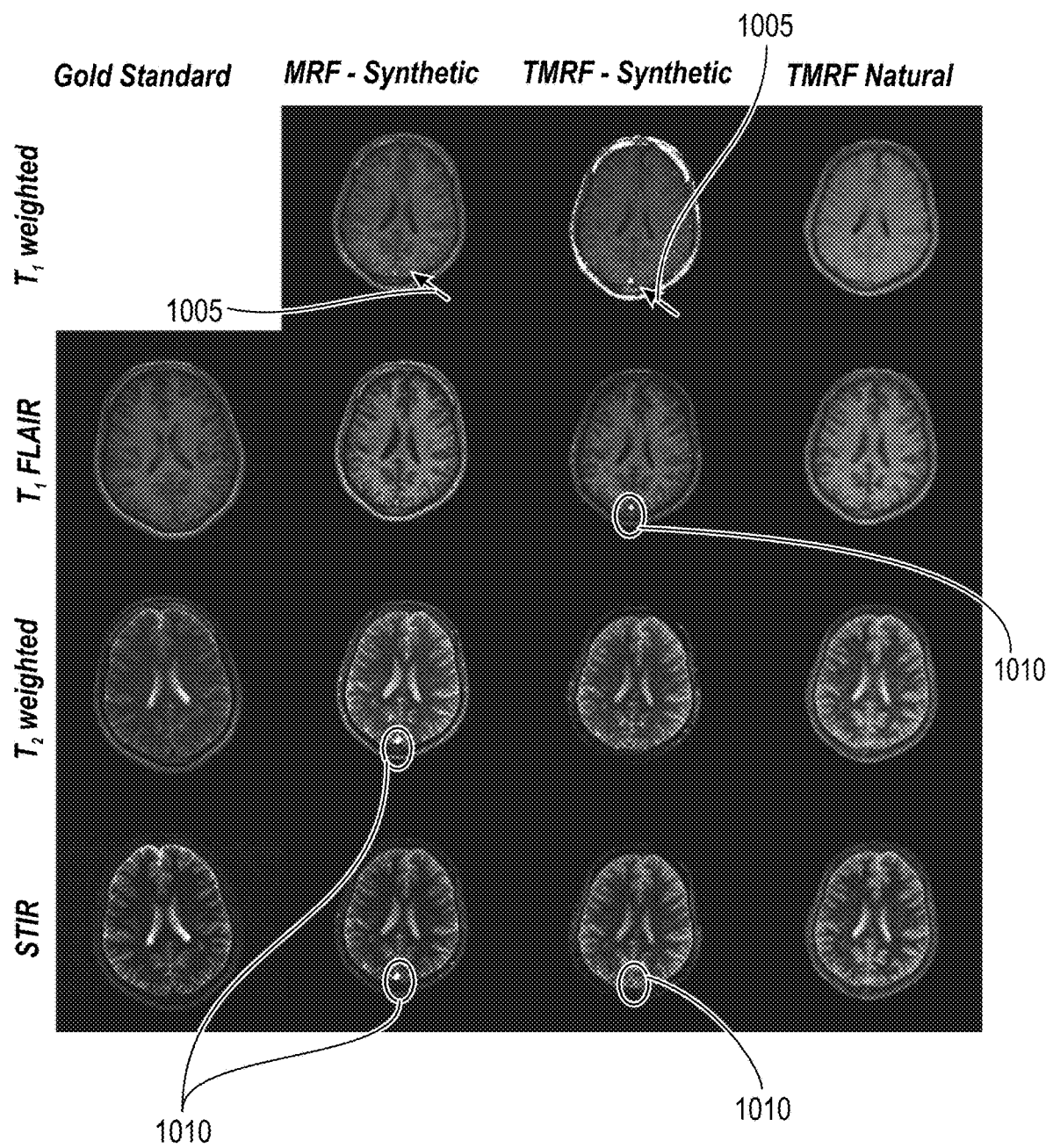
FIG. 10 is a set of exemplary reconstructed images according to an exemplary embodiment of the present disclosure.

Further Exemplary In Vivo Studies: Multi-contrast studies on healthy human brain. Simultaneous non-synthetic multi-contrast and quantitative images were rapidly acquired by tailoring: the MR fingerprinting acquisition schedule in contrast blocks. TMRF for five contrasts was designed, simulated and demonstrated on live healthy volunteers. FIG. 10 shows a set of exemplary reconstructed images acceding to an exemplary embodiment of the present disclosure for the GS, MRF synthetic contrast, TMRF synthetic contrast, and TMRF natural contrasts. Each row includes four different contrasts—$T_1$ weighted, $T_1$ FLAIR, $T_2$ weighted and Short T1 Inversion Recovery ("STIR"). Arrows 1005 and ellipses 1010 in the second and third columns indicate the flow artifacts (e.g., hyper-intensities or holes) which are not present in the GS and TMRF natural contrast images. The gold standard acquired was magnetization prepared $T_1$ weighted instead of $T_1$ weighted. All images were acquired on a 3T GE 750w scanner.

MRF and TMRF studies were performed on 4 normal volunteers. Both methods involved an axial, 20 slice brain coverage with a slice thickness of 5 mm, and 1 mm in plane resolution. GS sequences—$T_1$ weighted, $T_1$ FLAIR, $T_2$ weighted and STIR were acquired on the human brain. The spatio-temporal profiles of $T_1$, $T_2$, PD, water-fat and flow contrasts were reconstructed block-wise along with relaxometric maps. These MRF and TMRF maps were used to generate the synthetic contrast images using the signal equation and were compared. The TMRF natural contrast images were compared with the GS. FIG. 10 shows the representative images obtained from GS (e.g., natural contrast), MRF (e.g., synthetic contrast) and TMRF (e.g., synthetic and natural contrasts) for the following sequences—magnetization prepared $T_1$ weighted, $T_1$ FLAIR, $T_2$ weighted and STIR. The acquisition times for MRF and TMRF were 5:57 and 5:27 (min:sec) respectively.

Exemplary Image Quality

Exemplary ROI Analysis: Three ROIs each corresponding to WM, GM and CSF were manually drawn on the central slices (#9). The ROI masks were multiplied with the thousand-point time series of contrast images to obtain the mean ROI signal evolution of the three types of tissue matter for each of the volunteers for both schedules. These ROI mask were also multiplied with the parametric maps to obtain mean $T_1$, $T_2$ and PD values for each volunteer. A mean of means were computed for $T_1$, $T_2$ values for MRF and the TMRF schedules for the three types of tissue matter. The TMRF $T_1$ values for GM and WM can be higher compared to corresponding MRF values. However, these values can be within the range of $T_1$ values as reported in literature. The mean ROI values can be closely grouped across volunteers and corresponding values for the two schedules can be similar to one another.

Figure 11:
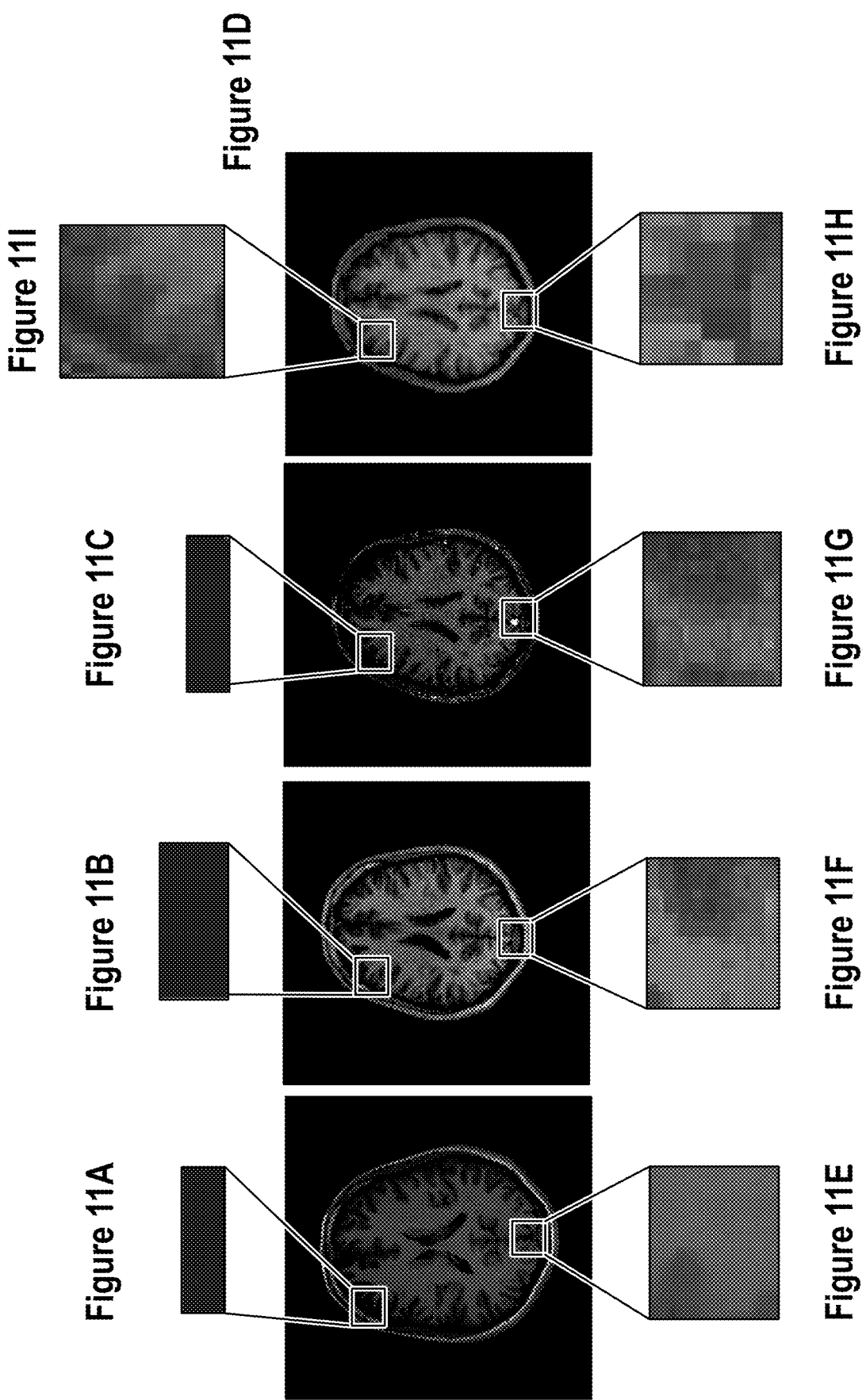
FIGS. 11A-11I are exemplary images comparing image quality according to an exemplary embodiment of the present disclosure.

Exemplary Image Analysis: FIGS. 11A-11I illustrate exemplary images comparing image quality according to an exemplary embodiment of the present disclosure. The synthetically generated images (e.g., MRF and TMRF) can be compared with the natural contrast images obtained from GS (see, e.g., FIGS. 11A-11D) and the TMRF images produced after sliding a window reconstruction as shown in FIGS. 11B-11D. The magnified version of the edges (e.g., between white matter and gray matter) and the presence/absence of flow artifact are shown in FIGS. 11E-11I. It can be observed that natural contrast from GS and TMRF can be resistant to flow artifact and also the boundaries can be smooth as compared to synthetic contrast. Additionally, the exemplary GS images can be similar to that of natural contrast obtained from TMRF. The data shown here can be representative $T_1$ FLAIR contrast and the results can be similar to other contrast.

The exemplary DIXON images obtained from the natural TMRF data do not suppress the water/fat accurately. The exemplary system, method and computer-accessible medium can optimize the DIXON method for better suppression of the fat and water. These optimized images can be compared with the LAVA Flex sequence.

The comparison of the image quality between the GS is shown in FIG. 11A, between exemplary synthetic images generated from MRF is shown in FIG. 11B, between synthetic images from TMRF is shown in FIG. 11C, and between natural images obtained after sliding windows reconstruction from TMRF is shown in FIG. 11C. All illustrated images are $T_1$ FLAIR contrast. A part of the image is magnified (e.g., as shown in the boxes) to see the effect of flow as shown in FIGS. 11E-11G and boundaries between gray matter and white matter, as shown in FIGS. 11H and 11I. The synthetic images shown in FIGS. 11H and 11I show pixelated and patchy behavior due to the fitting of a single tissue type per voxel as compared to those in FIGS. 11E-11G, which are smoother due to the absence of regression fits. Natural contrast obtained from GS and TMRF may not have any flow artifacts and can be another as compared to synthetic contrast data.

Exemplary Benefits of TMRF
1) Simultaneous non-synthetic multi-contrast and quantitative imaging.
2) Simple, quick and robust MRF protocol implementation that is flexible to include new contrasts such as water-fat imaging.
3) Challenges involving sliding window reconstruction along the temporal dimension due to constancy can be overcome.
4) Delivery of high insensitivity to flow artifacts caused by acquisition.
5) Sealable fingerprinting framework for tissue parameters measureable directly and indirectly with MRI—conductivity, temperature, etc.
6) Increased degrees of freedom in acquisition—randomization of trajectories, combination of sequence parameters for diverse contrasts such as, but not limited to, perfusion (e.g., contrast and non-contrast methods), diffusion, blood flow, etc.

7) Significant reduction in reconstruction computation times—as compared to analytical (including multiple variants of Fourier transform) methods relying on gridding or iterative reconstruction for non-Cartesian and/or under-sampled acquisitions.
8) Use of histopathological data as reference for fingerprints of pathology—training MRF sequences on stack of histopathological slides to understand the MRF signatures of such data.
9) Potential avoidance of biopsies in such anatomies.
10) Rapid comprehensive MRI exams, for example, pediatric neuroimaging, multi-parametric prostate imaging, whole body imaging oncology, diabetes studies inclusive of NASH, study of fat types such as brown, white and brite fat, etc.
11) MR value driven protocols, for example, 5-minute stroke protocol, as an alternate to EPImix, MAGIC, etc.
12) Multi-scale, multi-modality image fusion e.g., rapid MR-PET exams for oncological applications, whole body metabolic disorders and neuro-psychiatric diseases such as AD, PD, MS and SZ.
13) Atlas creation at higher field strengths to deliver increased information content at lower fields—synthesis of tissue parametric maps at higher fields could be utilized to train FCNs and employed for data generated from lower field strengths with appropriate correction factors that are field dependent.

Figure 12:
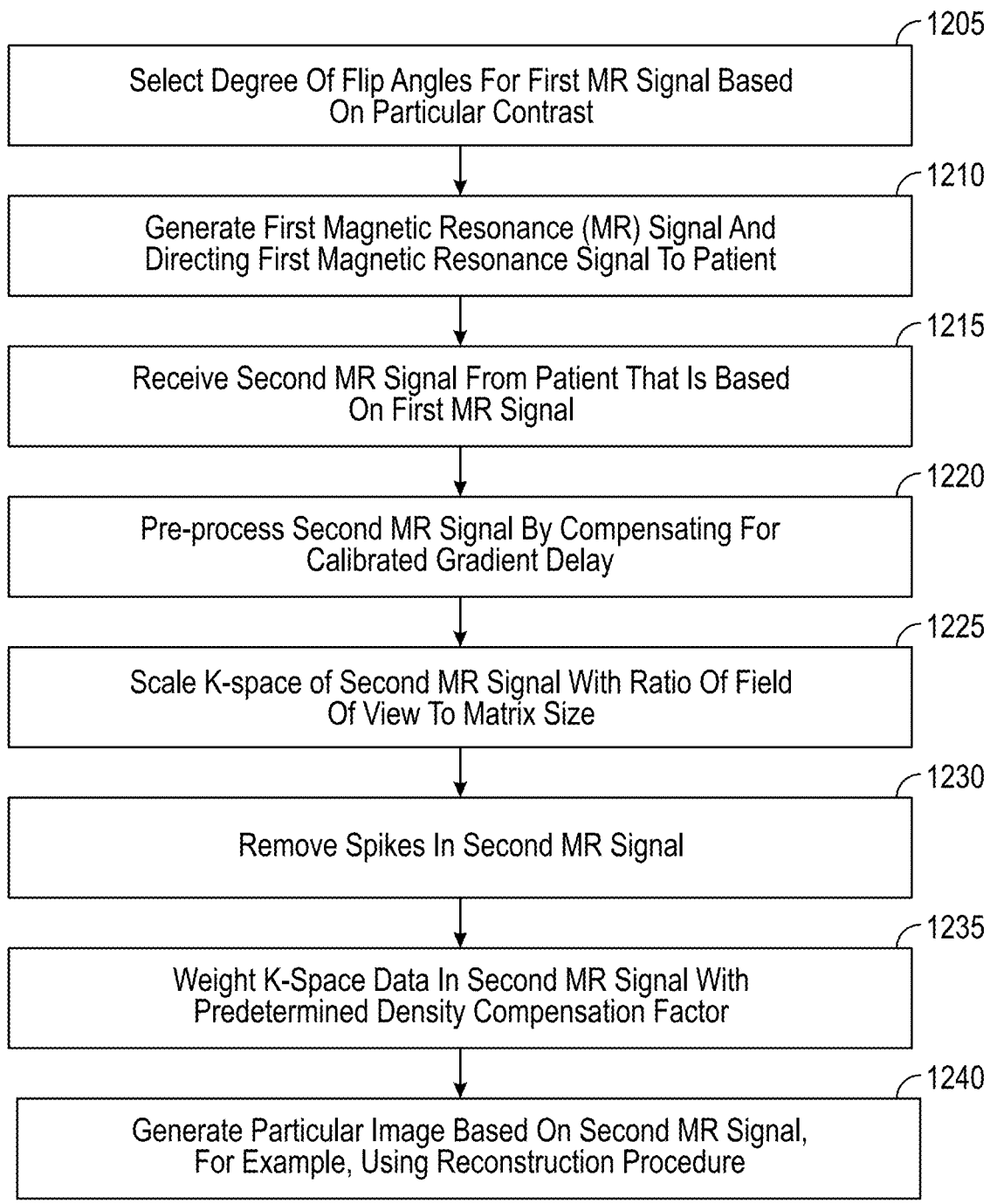
FIG. 12 is a flow diagram illustrating an exemplary method for generating a quantitative image of a patient or a non-synthetic contrast image of the patient according to an exemplary embodiment of the present disclosure.

FIG. 12 shows a flow diagram illustrating an exemplary method for generating a quantitative image of a patient or a non-synthetic contrast image of the patient according to an exemplary embodiment of the present disclosure. For example, at procedure 1205, a degree of flip angles for the first MR signal can be selected based on the particular contrast. At procedure 1210, a first magnetic resonance (MR) signal can be generated, which can be directed to the patient. At procedure 1215, a second MR signal can be received from the patient that can be based on the first MR signal. At procedure 1220, the second MR signal can be pre-processed by compensating for a calibrated gradient delay. At procedure 1225, k-space of the second MR signal can be scaled with a ratio of a field of view to a matrix size. At procedure 1230, spikes in the second MR signal can be removed. At procedure 1235, k-space data in the second MR signal can be weighted with a predetermined density compensation factor. At procedure 1240, the particular image can be generated based on the second MR signal, for example, using a reconstruction procedure.

Figure 13:
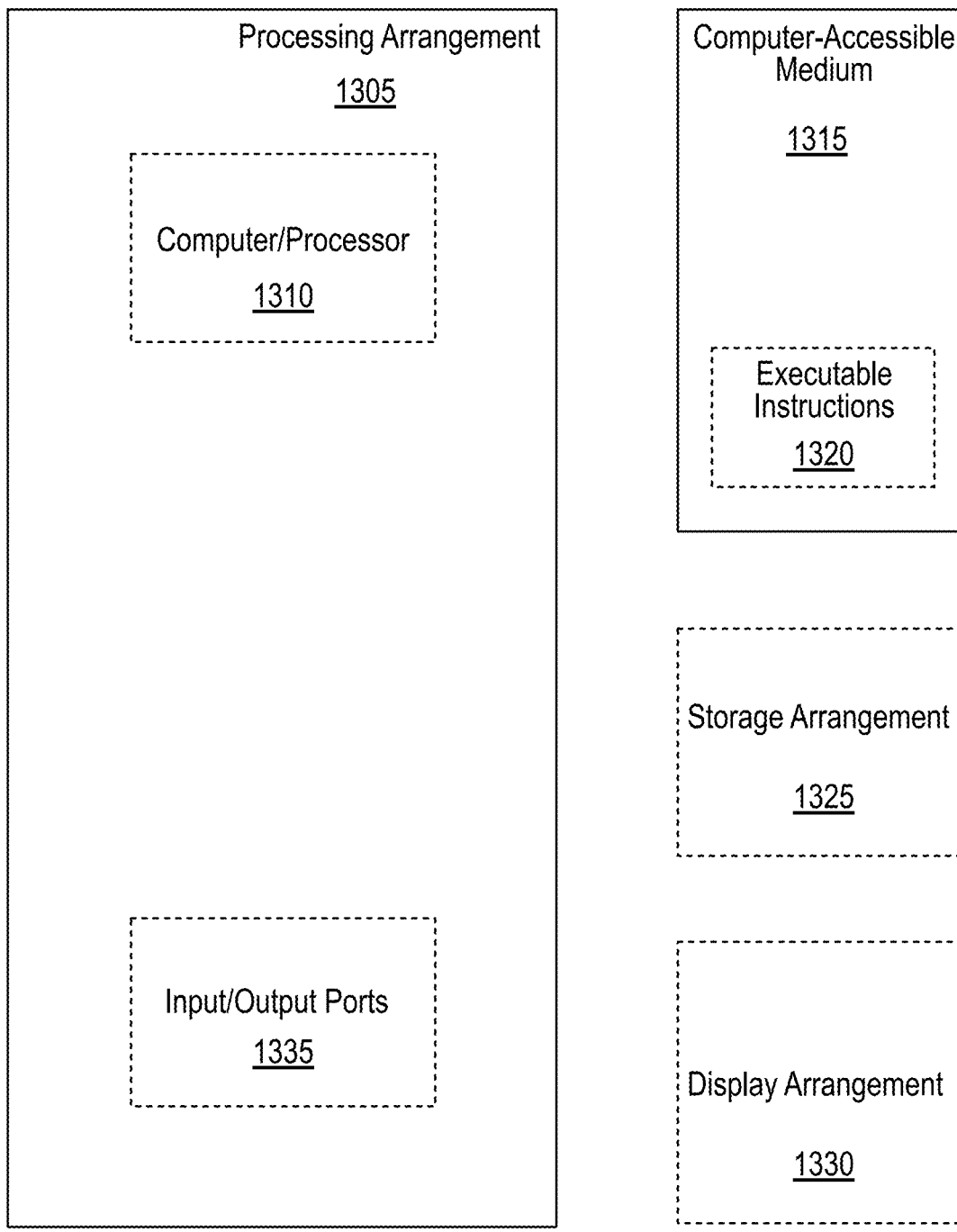
FIG. 13 is an illustration of an exemplary block diagram of an exemplary system in accordance with certain exemplary embodiments of the present disclosure.

FIG. 13 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1305. Such processing/computing arrangement 1305 can be, for example entirely or a part of, or include, but not limited to, a computer/processor 1310 that can include, for example one or more microprocessor, and use instructions stored on a computer-accessible medium (e.g., RAM, ROM, hard drive, or other storage device).

As shown in FIG. 13, for example a computer-accessible medium 1315 (e.g., as described herein above, a storage device such as a hard disk, floppy disk, memory stick, CD-ROM, RAM, ROM, etc., or a collection thereof) can be provided (e.g., in communication with the processing arrangement 1305). The computer-accessible medium 1315 can contain executable instructions 1320 thereon. In addition or alternatively, a storage arrangement 1325 can be provided separately from the computer-accessible medium 1315, which can provide the instructions to the processing arrangement 1305 so as to configure the processing arrangement to execute certain exemplary procedures, processes, and methods, as described herein above, for example.

Further, the exemplary processing arrangement 1305 can be provided with or include an input/output ports 1335, which can include, for example a wired network, a wireless network, the internet, an intranet, a data collection probe, a sensor, etc. As shown in FIG. 13, the exemplary processing arrangement 1305 can be in communication with an exemplary display arrangement 1330, which, according to certain exemplary embodiments of the present disclosure, can be a touch-screen configured for inputting information to the processing arrangement in addition to outputting information from the processing arrangement, for example. Further, the exemplary display arrangement 1330 and/or a storage arrangement 1325 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings, and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. Yankeeov T E, Abramson R G, Quarles C C. Quantitative multimodality imaging in cancer research and therapy. Nat. Rev. Clin. Oncol. 2014;11:670-680.
2. Abramson R, Burton K, John-Paul J, radiology ES-A, 2015 undefined. Methods and challenges in quantitative imaging biomarker development. Elsevier.
3. Doran S J. Chapter 21 Quantitative magnetic resonance imaging: applications and estimation of errors. Data Handl. Sci. Technol. 1996;118:4520488 doi: 10.1016/S0922-3487(96)80058-X.
4. Jara H. Theory of quantitative magnetic resonance imaging.
5. Seow P, Wong J H D, Ahmad-Anmar A, Mahajan A, Abdullah N A, Ramli N. Quantitative magnetic resonance imaging and radiogenomic biomarkers for glioma characterisation: a systematic review. Br. J. Radiol, 2018;91:20170930 doi: 10.1259/bjr.20170930.
6. Deoni S C L, Ratt B K, Peters T M. Rapid combined T1 and T2 mapping using gradient recalled acquisition in the steady state. Magn. Reson. Med. 2003;49:515-526 doi: 10.1002/mrm.10407.
7. Frost R, Jezzard P, Douaud G, Clare S, Porter D A, Miller K L. Scan time reduction for readout-segmented EPI using simultaneous multislice acceleration. Diffusion-weighted imaging at 3 and 7 Tesla. Magn. Reson. Med. 2015;74:136-149 doi: 10.1002/mrm.25391.
8. Shukla-Dave A, Obuchowski N A, Chenevert T L, et al. Quantitative imaging biomarkers alliance (QIBA) recommendations for improved precision of DW1 and DCE-MRI derived biomarkers in multicenter oncology trails. J. Magn. Reson. Imaging 2018 doi: 10.1002/jmri.26518.
9. Tanenbaum L N, Tsiouris A J, Johnson A N, et al. Synthetic MRI for clinical neuroimaging: results of the Magnetic Resonance Image Compilation (MAGiC) prospective, multicenter, multireader trial. Am. J. Neuroradiol. 2017.
10. Gonçalves F, Serai S, . . . . GZMR, 2018 undefined. Synthetic Brain MRI: Review of Current Concepts and Future Directions. journals.lww.com.
11. Ma D, Gulani V, Seiberlich N, et al. Magnetic resonance fingerprinting. Nature 2013 doi: 10.1038/nature11971.
12. Jang Y, Ma D, Seilberlich N, Gulani V, Griswold M A. MR fingerprinting using fast imaging with steady state precession (FISP) with spiral readout. Magn. Reson. Med. 2015;74:1621-1631 doi: 10.1002/mrm.25559.
13. Brown R, Haacke E, Cheng Y, Thompson M. Magnetic resonance imaging: physical principles and sequence design.; 2014.
14. Virtue P, Tamir J I, Doneva M, Yu S X, Lusting M. Learning Contrast Synthesis from MR Fingerprinting.
15. Hänicke W, Vogel H U. An analytical solution for the SSFP signal in MRI. Magn. Reson. Med. 2003;49:771-775 doi: 10.1002/mrm.10410.
16. Berstein M a., King K F, Zhou X J. Handbook of MRI Pulse Sequences, Appendix II.; 2004. doi: 10.1016/B978-012092861-3/50026-1.
17. Weigel M. Extended phase graphs: Dephasing RF pulses, and echoes—pure and simple. J. Magn. Reson. Imaging 2015;41:266-295 doi: 10.1002/jmri.24619.
18. Cao X., Liao C., Wang Z., et al. Robust sliding-window reconstruction for Accelerating the acquisition of MR fingerprinting. Magn. Reson. Med. 2017;78: 1579-1588 doi: 10.1002/mrm.26521.
19. Fessler J. Image reconstruction toolbox. Available at website http://www.eecs.umich.edu/fessler/code 2012 doi: 10.1007/978-0-387-85922-4.
20. Dixon W T. Simple proton spectroscopic imaging. Radiology 1984;153:189-194 doi: 10.1148/radiology.153.1.6089263.
21. Wansapura J P, Holland S K, Duan R S, Ball W S. NMR relaxation times in the human brain at 3.0 tesla. J. Magn. Reson. Imaging 1999;9:531-538 doi: 10.1002/(SICI)1522-2586(199904)9:4<531×AID-JMRI4>3.0, CO;2-L.
22. Wansapura J P, Holland S K, Duan R S, Ball W S. NMR relaxation times in the human brain at 3.0 tesla. J. Magn. Reson. Imaging 1999;9:531-538 doi: 10.1002/(SICI)1522-2586(199904)9:4<531×AID-JMRI4>3.0, CO;2-L.
23. Smith S M, Jenkinson M, Woolrich M W, et al. Advances in functional and structural MR image analysis and implementation as FSL. Neuroimage 2004;23: S208-S219 doi: 10.1016/J.NEUROIMAGE.2004.07.051.
24. Reeder S B, Mckenzie C A, Pineda, A R, et al. Water-fat separation with IDEAL gradient-echo imaging. J. Magn. Reson. Imaging 2007;25:644-62 doi: 10.1002/jmri.20831.).
25. Ravi, K. S., Geethanath, S., Jochen, W., & Vaughan, J. T. (2018a). MR value driven autonomous mri using imr-franework. In ISMRM workshop on machine learning part ii, Washington, D.C.
26. Ravi, K. S., Geethanath, S., & Vaughan, J. T. (2018b). Imr-framework for rapid design and deployment of non-cartesian sequences. In I2i workshop Retrieved from cai2r.net/i2i.
27. Ravi, K. S., Geethanath, S., & Vaughan, J. T. (2019a). Autonomous scanning using imr framework to improve mr accessibility. In ISMRM workshop on accessible mri for the world. New Delhi, India.
28. Ravi, K. S., Geethanath, S., & Vaughan, J. T. (2019b). Self-administrated exam using autonomous magnetic resonance imaging (amri). In ISMRM 27th annual meeting and exhibition. Montreal, Canada.
29. Ravi, K. S., Potdar, S., Poojar, P., Reddy, A. K., Kroboth, S., Nielsen, J.-F., Zaitsev, M., et al. (2018). Pulseq graphical programming interface: Open source visual environment for prototyping pulse sequence and integrated magnetic resonance imaging algorithm development. Magnetic resonance imaging; 52, 9-15. doi:10.1016/j.mri.2018.03.008.
30. Keerthi Sravan Ravi, Sairam Geethanath, Girish Srinivasan, Rahul Sharma, Sachin R. Jambawalikar, Angela Lignelli-Dipple, and John Thomas Vaughan Jr. Deep learning Assisted Raidological reporT (DART). In ISMRM 28th Annual. Meeting & Exhibition in Sydney, Australia.
31. Keerthi Sravan Ravi, Sairam Geethanath, Patrick Quarterman, Maggie Fung, John Thomas Vaughan Jr., "Intelligent Protocoling for Antonormous MRI". ISMRM Annual Meeting & Exhibition. ISMRM, 2020.

What is claimed is:

1. A non-transitory computer-accessible medium having stored thereon computer-executable instructions for generating at least one particular image which is at least one of (i) at least one quantitative image of at least one section of at least one patient or (ii) at least one non-synthetic contrast image of the at least one section of the at least one patient, wherein, when a computer arrangement executes the instructions, the computer arrangement is configured to perform procedures comprising:

generating a first magnetic resonance (MR) signal and directing the first MR signal to the at least one patient;
receiving a second MR signal from the at least one patient that is based on the first MR signal;
generating the at least one particular image based on the second MR signal; and
generating MR information based on the second MR signal by:
pre-processing the second MR signal by compensating for a calibrated gradient delay,
scaling k-space of the second MR signal with a ratio of a field of view to a matrix size,
removing spikes in the second MR signal, and
weighting k-space data in the second MR signal with a predetermined density compensation factor, wherein the at least one particular image is generated based on the MR information.

2. The computer-accessible medium of claim 1, wherein the first MR signal is a configured MR signal.

3. The computer-accessible medium of claim 2, wherein the MR signal is configured for a particular contrast.

4. The computer-accessible medium of claim 3, wherein the first MR signal has a constant signal intensity.

5. The computer-accessible medium of claim 4, wherein the computer arrangement is configured to generate the first MR signal based on a degree of a plurality of flip angles that maintains the constant signal intensity.

6. The computer-accessible medium of claim 3, wherein the computer arrangement is configured to select a degree of flip angles for the first MR signal based on the particular contrast.

7. The computer-accessible medium of claim 6, wherein the degree of the flip angles varies within a particular range.

8. The computer-accessible medium of claim 7, wherein the degree of the flip angles varies about a mean value.

9. The computer-accessible medium of claim 8, wherein the degree of the flip angles varies monotonously about the mean value.

10. The computer-accessible medium of claim 7, wherein the degree of the flip angles varies pseudo randomly within the particular range.

11. The computer-accessible medium of claim 7, wherein the particular range is about -−5+/−4 degrees, about 45+/−5 degrees, about 75+/−5 degrees, or about 75+/−5 degrees.

12. The computer-accessible medium of claim 3, wherein the particular contrast includes at least one of T1, T2, proton density, water, fat, off resonance, diffusion, perfusion, or flow.

13. The computer-accessible medium of claim 1, wherein the at least one non-synthetic contrast image is at least one non-synthetic multi-contrast image.

14. The computer-accessible medium of claim 1, wherein the computer arrangement is configured to generate the at least one particular image using a reconstruction procedure.

15. The computer-accessible medium of claim 14, wherein the reconstruction procedure is a sliding window reconstruction procedure.

16. The computer-accessible medium of claim 15, wherein the reconstruction procedure includes converting the second MR signal to an image using a Non-Uniform Fast Fourier Transform.

17. The computer-accessible medium of claim 1, wherein the computer arrangement is configured to generate the at least one quantitative image by vector-dot product matching $L_2$-norm normalized dictionary entries with voxel signal evolutions in the second MR signal.

18. A method for generating at least one particular image which is at least one of (i) at least one quantitative image of at least one section of at least one patient or (ii) at least one non-synthetic contrast image of the at least one section of the at least one patient, comprising:
  generating a first magnetic resonance (MR) signal and directing the first MR signal to the at least one patient;
  receiving a second MR signal from the at least one patient that is based on the first MR signal;
  generating the at least one particular image based on the second MR signal; and
  generating MR information based on the second MR signal by:
    pre-processing the second MR signal by compensating for a calibrated gradient delay,
    scaling k-space of the second MR signal with a ratio of a field of view to a matrix size,
    removing spikes in the second MR signal, and
    weighting k-space data in the second MR signal with a predetermined density compensation factor,
  wherein the at least one particular image is generated based on the MR information.

19. A system for generating at least one particular image which is at least one of (i) at least one quantitative image of at least one section of at least one patient or (ii) at least one non-synthetic contrast image of the at least one section of the at least one patient, comprising:
  a computer hardware arrangement configured to:
    generate a first magnetic resonance (MR) signal and directing the first MR signal to the at least one patient;
    receive a second MR signal from the at least one patient that is based on the first MR signal; and
  generate the at least one particular image based on the second MR signal; and
  generate MR information based on the second MR signal by:
    pre-processing the second MR signal by compensating for a calibrated gradient delay,
    scaling k-space of the second MR signal with a ratio of a field of view to a matrix size,
    removing spikes in the second MR signal, and
    weighting k-space data in the second MR signal with a predetermined density compensation factor,
  wherein the at least one particular image is generated based on the MR information.

* * * * *